United States Patent
Noureldin et al.

(10) Patent No.: US 9,915,477 B2
(45) Date of Patent: Mar. 13, 2018

(54) RECOVERY AND RE-USE OF WASTE ENERGY IN INDUSTRIAL FACILITIES

(71) Applicant: Saudi Arabian Oil Company, Dhahran (SA)

(72) Inventors: Mahmoud Bahy Mahmoud Noureldin, Dhahran (SA); Hani Mohammed Al Saed, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 0 days.

(21) Appl. No.: 15/242,100

(22) Filed: Aug. 19, 2016

(65) Prior Publication Data
US 2017/0058208 A1  Mar. 2, 2017

Related U.S. Application Data

(60) Provisional application No. 62/209,217, filed on Aug. 24, 2015, provisional application No. 62/209,147, (Continued)

(51) Int. Cl.
*F28D 7/00* (2006.01)
*C10G 45/02* (2006.01)
(Continued)

(52) U.S. Cl.
CPC .......... *F28D 7/0083* (2013.01); *B01D 3/007* (2013.01); *B01D 3/32* (2013.01); *B01D 51/10* (2013.01);
(Continued)

(58) Field of Classification Search
CPC ........ C10G 35/04; C10G 45/02; C10G 45/44; F28F 9/26; B01D 3/007; B01D 3/32;
(Continued)

(56) References Cited

U.S. PATENT DOCUMENTS 3,995,428 A   12/1976 Roberts
4,109,469 A   8/1978 Carson
(Continued)

FOREIGN PATENT DOCUMENTS

CN    1844325    10/2006
CN    101424453  5/2009
(Continued)

OTHER PUBLICATIONS

Schaschke, C. (2014) A Dictionary of Chemical Engineering, Oxford Univeristy Press, 448 pgs (Office action cites Tatoray process).*

(Continued)

*Primary Examiner* — Brian McCaig
(74) *Attorney, Agent, or Firm* — Fish & Richardson P.C.

(57) ABSTRACT

Configurations and related processing schemes of specific inter-plants and hybrid, intra- and inter-plants waste heat recovery schemes for thermal energy consumption reduction in integrated refining-petrochemical facilities synthesized for grassroots medium grade crude oil semi-conversion refineries to increase energy efficiency from specific portions of low grade waste heat sources are described. Configurations and related processing schemes of specific inter-plants and hybrid, intra- and inter-plants waste heat recovery schemes for thermal energy consumption reduction in integrated refining-petrochemical facilities synthesized for integrated medium grade crude oil semi-conversion refineries and aromatics complex for increasing energy efficiency from specific portions of low grade waste sources are also described.

22 Claims, 31 Drawing Sheets

Related U.S. Application Data filed on Aug. 24, 2015, provisional application No. 62/209,188, filed on Aug. 24, 2015, provisional application No. 62/209,223, filed on Aug. 24, 2015.

(51) Int. Cl.

| | | |
|---|---|---|
| *F28F 9/26* | (2006.01) | |
| *C10G 45/44* | (2006.01) | |
| *C10G 35/04* | (2006.01) | |
| *B01D 3/32* | (2006.01) | |
| *B01D 53/047* | (2006.01) | |
| *C10L 3/10* | (2006.01) | |
| *C07C 7/08* | (2006.01) | |
| *C10G 65/12* | (2006.01) | |
| *C10G 33/06* | (2006.01) | |
| *B01D 3/00* | (2006.01) | |
| *B01D 51/10* | (2006.01) | |
| *B01D 53/14* | (2006.01) | |
| *B01D 53/18* | (2006.01) | |
| *B01D 53/34* | (2006.01) | |
| *B01D 53/48* | (2006.01) | |
| *B01D 53/86* | (2006.01) | |
| *B01D 53/96* | (2006.01) | |
| *C02F 1/58* | (2006.01) | |
| *C10G 47/00* | (2006.01) | |
| *C10G 65/00* | (2006.01) | |
| *F01D 17/14* | (2006.01) | |
| *F01K 3/18* | (2006.01) | |
| *F01K 13/02* | (2006.01) | |
| *H02K 7/18* | (2006.01) | |
| *C10G 69/00* | (2006.01) | |
| *F01K 25/06* | (2006.01) | |
| *F01K 25/08* | (2006.01) | |
| *F01K 27/02* | (2006.01) | |
| *F01K 13/00* | (2006.01) | |
| *F01K 23/06* | (2006.01) | |
| *C01B 3/24* | (2006.01) | |
| *C10G 45/00* | (2006.01) | |
| *C10K 3/04* | (2006.01) | |
| *F01K 27/00* | (2006.01) | |
| *C02F 101/10* | (2006.01) | |
| *C02F 101/16* | (2006.01) | |
| *C02F 103/18* | (2006.01) | |
| *C02F 103/36* | (2006.01) | |

(52) U.S. Cl.
CPC ....... *B01D 53/047* (2013.01); *B01D 53/1462* (2013.01); *B01D 53/185* (2013.01); *B01D 53/343* (2013.01); *B01D 53/48* (2013.01); *B01D 53/8603* (2013.01); *B01D 53/96* (2013.01); *C01B 3/24* (2013.01); *C02F 1/586* (2013.01); *C07C 7/08* (2013.01); *C10G 33/06* (2013.01); *C10G 35/04* (2013.01); *C10G 45/00* (2013.01); *C10G 45/02* (2013.01); *C10G 45/44* (2013.01); *C10G 47/00* (2013.01); *C10G 65/00* (2013.01); *C10G 65/12* (2013.01); *C10G 69/00* (2013.01); *C10K 3/04* (2013.01); *C10L 3/101* (2013.01); *C10L 3/103* (2013.01); *C10L 3/104* (2013.01); *F01D 17/145* (2013.01); *F01K 3/185* (2013.01); *F01K 13/00* (2013.01); *F01K 13/02* (2013.01); *F01K 23/06* (2013.01); *F01K 23/064* (2013.01); *F01K 25/06* (2013.01); *F01K 25/08* (2013.01); *F01K 27/00* (2013.01); *F01K 27/02* (2013.01); *F28F 9/26* (2013.01); *H02K 7/1823* (2013.01); *B01D 2252/204* (2013.01); *C01B 2203/0233* (2013.01); *C02F 2101/10* (2013.01); *C02F 2101/101* (2013.01); *C02F 2101/16* (2013.01); *C02F 2103/18* (2013.01); *C02F 2103/36* (2013.01); *C10G 2300/202* (2013.01); *C10G 2300/207* (2013.01); *C10G 2300/4006* (2013.01); *C10G 2300/4056* (2013.01); *C10G 2400/04* (2013.01); *C10G 2400/30* (2013.01); *C10L 2290/06* (2013.01); *C10L 2290/541* (2013.01); *Y02P 20/129* (2015.11)

(58) Field of Classification Search
CPC .............. B01D 53/047; B01D 53/1462; B01D 53/185; B01D 53/343; B01D 53/48; B01D 53/8603; B01D 53/96
See application file for complete search history.

(56) References Cited

U.S. PATENT DOCUMENTS

| | | | |
|---|---|---|---|
| 4,291,232 A | 9/1981 | Cardone | |
| 4,471,619 A | 9/1984 | Nolley, Jr. | |
| 4,512,155 A | 4/1985 | Sheinbaum | |
| 4,792,390 A | 12/1988 | Staggs | |
| 4,962,238 A | 10/1990 | Wolfe | |
| 5,007,240 A | 4/1991 | Ishida | |
| 5,164,070 A | 11/1992 | Munro | |
| 5,240,476 A | 8/1993 | Hegarty | |
| 5,497,624 A | 3/1996 | Amir | |
| 6,733,636 B1 | 5/2004 | Heins | |
| 8,046,999 B2 | 11/2011 | Doty | |
| 9,328,634 B2 | 5/2016 | Ikegami | |
| 9,562,201 B2 | 2/2017 | Noureldin | |
| 2002/0023538 A1 | 2/2002 | Agarwal | |
| 2003/0092952 A1* | 5/2003 | Netzer | C10G 69/12 585/648 |
| 2003/0132138 A1 | 7/2003 | Mehra | |
| 2004/0186332 A1* | 9/2004 | Kong | C07C 6/123 585/475 |
| 2006/0010872 A1 | 1/2006 | Singh | |
| 2008/0128134 A1 | 6/2008 | Mudunuri | |
| 2008/0174115 A1 | 7/2008 | Lambirth | |
| 2008/0257413 A1 | 10/2008 | Noureldin et al. | |
| 2008/0289588 A1 | 11/2008 | Wees et al. | |
| 2008/0314726 A1 | 12/2008 | Choros | |
| 2009/0000299 A1 | 1/2009 | Ast | |
| 2009/0000906 A1 | 1/2009 | Petri | |
| 2009/0071652 A1 | 3/2009 | Vinegar | |
| 2009/0225929 A1 | 9/2009 | Genta et al. | |
| 2009/0287029 A1 | 11/2009 | Anumakonda et al. | |
| 2009/0301087 A1 | 12/2009 | Borissov et al. | |
| 2010/0146974 A1 | 6/2010 | Ast | |
| 2010/0242476 A1 | 9/2010 | Ast | |
| 2010/0263380 A1 | 10/2010 | Biederman | |
| 2010/0319346 A1 | 12/2010 | Ast | |
| 2010/0326076 A1 | 12/2010 | Ast | |
| 2011/0016863 A1 | 1/2011 | Ernst | |
| 2011/0072819 A1 | 3/2011 | Silva | |
| 2011/0072820 A1 | 3/2011 | Finkenrath | |
| 2011/0083437 A1 | 4/2011 | Ast | |
| 2011/0158858 A1 | 6/2011 | Alves | |
| 2012/0031096 A1 | 2/2012 | Acikgoz et al. | |
| 2012/0047889 A1 | 3/2012 | Acikgoz et al. | |
| 2012/0048718 A1 | 3/2012 | Werba | |
| 2012/0085096 A1 | 4/2012 | Penton et al. | |
| 2012/0131921 A1 | 5/2012 | Held | |
| 2012/0279728 A1 | 11/2012 | Northrop | |
| 2012/0279900 A1 | 11/2012 | Noureldin et al. | |
| 2012/0285169 A1 | 11/2012 | Freund | |
| 2012/0298552 A1 | 11/2012 | Koseoglu | |
| 2013/0104546 A1 | 5/2013 | Goswami | |
| 2013/0145763 A1 | 6/2013 | Mirmobin et al. | |
| 2013/0165534 A1 | 6/2013 | McComish | |
| 2013/0213040 A1 | 8/2013 | Goswami | |
| 2013/0231909 A1 | 9/2013 | Noureldin | |

(56) References Cited

U.S. PATENT DOCUMENTS

| | | |
|---|---|---|
| 2013/0238154 A1 | 9/2013 | Noureldin |
| 2013/0334060 A1 | 12/2013 | Koseoglu et al. |
| 2014/0090405 A1 | 4/2014 | Held et al. |
| 2014/0142364 A1 | 5/2014 | Io |
| 2014/0260311 A1 | 9/2014 | Berlowitz |
| 2015/0377079 A1 | 12/2015 | Noureldin |
| 2016/0045841 A1 | 2/2016 | Kaplan |

FOREIGN PATENT DOCUMENTS

| | | |
|---|---|---|
| CN | 104560082 | 4/2015 |
| DE | 3731978 A1 | 3/1988 |
| EP | 0292391 | 11/1988 |
| EP | 949318 | 10/1999 |
| EP | 2516326 | 10/2012 |
| FR | 2990990 | 11/2013 |
| SU | 295317 | 10/1977 |
| WO | 97/21786 | 6/1997 |
| WO | 2004102082 | 11/2004 |
| WO | WO2011/090553 A1 | 7/2011 |
| WO | 2012048132 | 4/2012 |
| WO | 2013055864 | 4/2013 |
| WO | WO2014/205163 A1 | 12/2014 |

OTHER PUBLICATIONS

Marcilly, C. (2005) Acido-Basic Catalysis: Applications to Refining and Petrochemistry, IFP Publications, 896 pgs (Office action cites pp. 512-513).*

Gary, J.H. et al. (2007) Petroleum Refining Technology and Economics, $5^{th}$ ed., CRC Press, 463 pgs (Office action cites p. 3).*

PCT International Search Report and Written Opinion of the International Searching Authority, PCT/US2016/048074, November 9, 2016, 12 pages.

PCT International Search Report and Written Opinion of the International Searching Authority, PCT/US2016/048042, Nov. 9, 2016, 12 pages.

Feng Xu, D. Yogi Goswami and Sunil S. Bhagwat, "A combined power/cooling cycle," Energy, 25 (2000), 233-246.

D. Zheng, B. Chen, Y. Qi and H. Jin, "Thermodynamic analysis of a novel absorption power/cooling combined cycle," Applied Energy, 83 (2006), 311-323.

Meng Liu, and Na Zhang, "Proposal and analysis of a novel ammonia-water cycle for power and refrigeration cogeneration," Energy, 32 (2007), 961-970.

J.Wang, Y. Dai and L. Gao, "Parametric analysis and optimization for a combined power and refrigeration cycle," Applied Energy, 85 (2008), 1071-1085.

R.V. Padilla, G. Demirkaya, D. Yogi Goswami, E. Stefanakos, and M. A. Rahman, "Analysis of power and cooling cogeneration using ammonia-water mixture," Energy, 35 (2010), 4649-4657.

D. Ayou, J. C. Bruno, R. Saravanan and A. Coronas, "An Overview of Combined Absorption Power and Cooling Cycles," Renewable sustainable energy reviews, 21 (2013), 728-748.

J. Hua, Y. Chen, Y. Wang and A.P. Roskilly, "Thermodynamic analysis of ammonia-water power/chilling cogeneration cycle with low grade waste heat," Applied thermal engineering , 64 (2014), 483-490.

Hasan et al., "First and Second Law Analysis of a New Power and Refrigeration Thermodynamic Cycle using a Solar Heat Source," Pergamon, Solar Energy, vol. 73, No. 5, Nov. 1, 2002, pp. 385-393.

Stecco, "Kalea Cycles: Some Possible Applications and Comments," Proceedings of the American Power Conference, XP 000609703, Jan. 1, 1993, vol. 1, pp. 196-201.

Tamm et al., "Theoretical and Experimental Investigation of an Ammonia-Water Power and Refrigeration Thermodynamic Cycle," Science Direct, Solar Energy, vol. 76, No. 1-3, Jan. 1, 2004, pp. 217-228.

Sadrameli et al., "Optimum Operating Conditions for a Combined Power and Cooling Thermodynamic Cycle," Science Direct, Applied Energy, vol. 84, No. 3, Nov. 10, 2006, pp. 254-265.

Vidal, "Analysis of a Combined Power and Refrigeration Cycle by the Energy Method," Science Direct, Energy 31, Dec. 1, 2006, pp. 3401-3414.

PCT International Search Report and Written Opinion of the International Searching Authority, PCT/US2016/027417, dated Jul. 6, 2016, 11 pages.

PCT International Search Report and Written Opinion of the International Searching Authority, PCT/US2016/027797, dated Oct. 19, 2016, 12 pages.

PCT International Search Report and Written Opinion of the International Searching Authority, PCT/US2016/027794, dated Oct. 19, 2016, 13 pages.

PCT International Search Report and Written Opinion of the International Searching Authority, PCT/US2016/030063, dated Oct. 19, 2016, 13 pages.

PCT International Search Report and Written Opinion of the International Searching Authority, PCT/US2016/030156, dated Oct. 19, 2016, 12 pages.

PCT International Search Report and Written Opinion of the International Searching Authority, PCT/US2016/048067, dated Nov. 15, 2016, 11 pages.

PCT International Search Report and Written Opinion of the International Searching Authority, PCT/US2016/048066, dated Nov. 15, 2016, 11 pages.

PCT International Search Report and Written Opinion of the International Searching Authority, PCT/US2016/048078, dated Nov. 15, 2016, 12 pages.

PCT International Search Report and Written Opinion of the International Searching Authority, PCT/US2016/048076, dated Nov. 15, 2016, 12 pages.

PCT International Search Report and Written Opinion of the International Searching Authority, PCT/US2016/048207, dated Nov. 21, 2016, 12 pages.

PCT International Search Report and Written Opinion of the International Searching Authority, PCT/US2016/048219, dated Nov. 21, 2016, 13 pages.

PCT International Search Report and Written Opinion of the International Searching Authority, PCT/US2016/048229, dated Nov. 21, 2016, 13 pages.

PCT International Search Report and Written Opinion of the International Searching Authority, PCT/US2016/048236, dated Nov. 21, 2016, 13 pages.

PCT International Search Report and Written Opinion of the International Searching Authority, PCT/US2016/027413, dated Nov. 22, 2016, 11 pages.

PCT International Search Report and Written Opinion of the International Searching Authority, PCT/US2016/048063, dated Nov. 23, 2016, 11 pages.

PCT International Search Report and Written Opinion of the International Searching Authority, PCT/US2016/048071, dated Nov. 23, 2016, 11 pages.

PCT International Search Report and Written Opinion of the International Searching Authority, PCT/US2016/048210, dated Dec. 22, 2016, 11 pages.

PCT International Search Report and Written Opinion of the International Searching Authority, PCT/US2016/048224, dated Dec. 22, 2016, 11 pages.

PCT International Search Report and Written Opinion of the International Searching Authority, PCT/US2016/048209, dated Dec. 22, 2016, 11 pages.

PCT International Search Report and Written Opinion of the International Searching Authority, PCT/US2016/048237, dated Dec. 22, 2016, 11 pages.

PCT International Search Report and Written Opinion of the International Searching Authority, PCT/US2016/048223, dated Dec. 22, 2016, 11 pages.

PCT International Search Report and Written Opinion of the International Searching Authority, PCT/US2016/048212, dated Dec. 22, 2016, 11 pages.

* cited by examiner

RECOVERY AND RE-USE OF WASTE ENERGY IN INDUSTRIAL FACILITIES

CROSS-REFERENCE TO RELATED APPLICATIONS

This application claims priority under 35 U.S.C. § 119 to U.S. Provisional Patent Application Ser. No. 62/209,217, filed on Aug. 24, 2015; U.S. Provisional Patent Application Ser. No. 62/209,147, filed on Aug. 24, 2015; U.S. Provisional Patent Application Ser. No. 62/209,188, filed on Aug. 24, 2015; and U.S. Provisional Patent Application Ser. No. 62/209,223, filed on Aug. 24, 2015. The entire contents of each of the preceding applications are incorporated herein by reference in their respective entireties.

TECHNICAL FIELD

This specification relates to operating industrial facilities, for example, crude oil refining facilities or other industrial facilities that include operating plants that generate heat.

BACKGROUND

Petroleum refining processes are chemical engineering processes and other facilities used in petroleum refineries to transform crude oil into products, for example, liquefied petroleum gas (LPG), gasoline, kerosene, jet fuel, diesel oils, fuel oils, and other products. Petroleum refineries are large industrial complexes that involve many different processing units and auxiliary facilities, for example, utility units, storage tanks, and other auxiliary facilities. Each refinery can have its own unique arrangement and combination of refining processes determined, for example, by the refinery location, desired products, economic considerations, or other factors. The petroleum refining processes that are implemented to transform the crude oil into the products such as those listed earlier can generate heat, which may not be reused, and byproducts, for example, greenhouse gases (GHG), which may pollute the atmosphere. It is believed that the world's environment has been negatively affected by global warming caused, in part, due to the release of GHG into the atmosphere.

SUMMARY

This specification describes technologies relating to specific direct or indirect inter-plants and hybrid, intra- and inter-plants integration for energy consumption reduction from waste energy in industrial facilities.

The details of one or more implementations of the subject matter described in this specification are set forth in the accompanying drawings and the description later. Other features, aspects, and advantages of the subject matter will become apparent from the description, the drawings, and the claims.

BRIEF DESCRIPTION OF THE DRAWINGS

FIGS. 1P-1AC illustrate configurations and related scheme details for thermally integrating different refining plants in the crude oil refining facility.

DETAILED DESCRIPTION

Figure 1A:
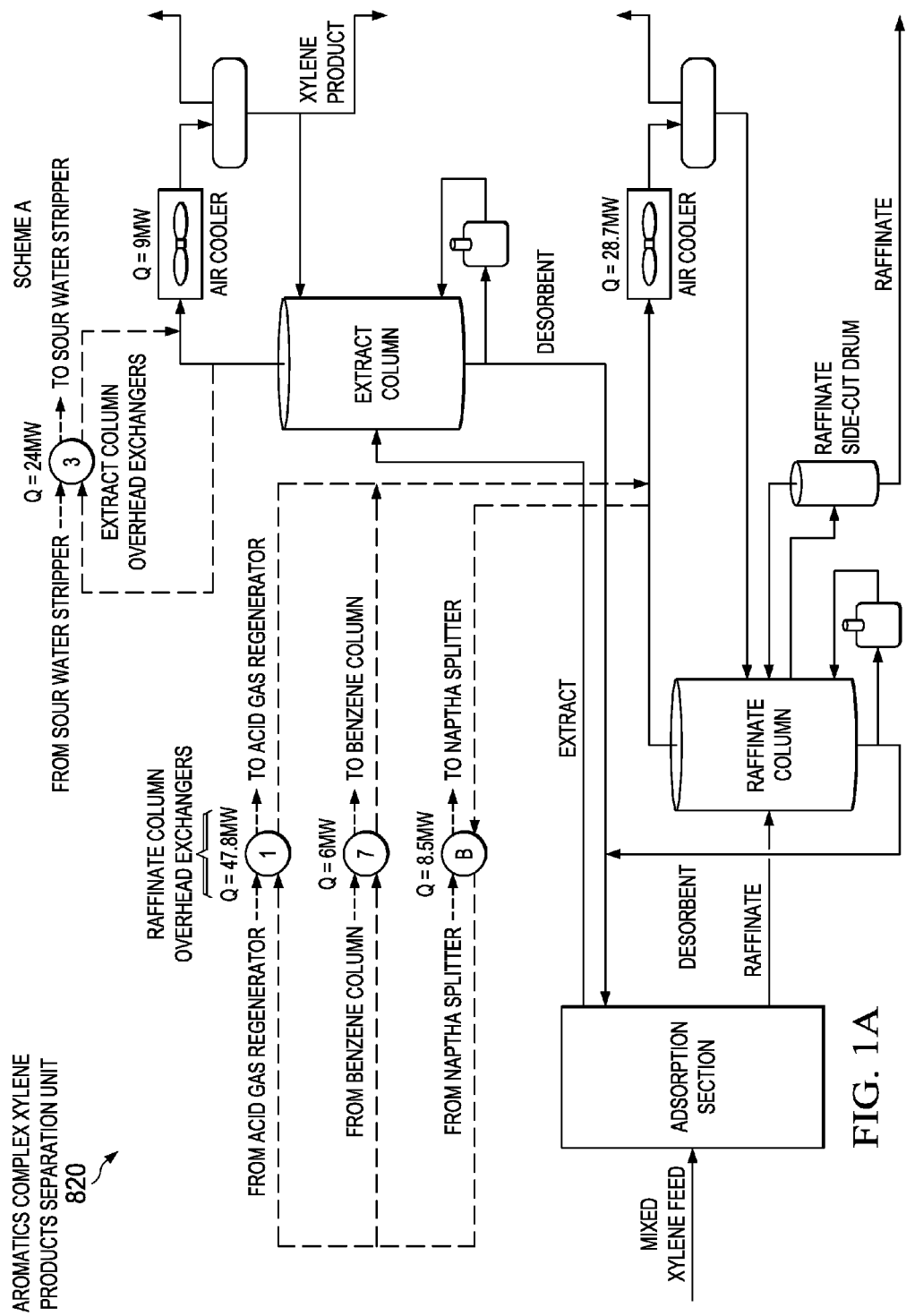
FIGS. 1A-1O illustrate configurations and related scheme details for thermally integrating different refining plants in the crude oil refining facility.

Industrial waste heat is a source for potential carbon-free power generation in many industrial facilities, for example, crude oil refineries, petrochemical and chemical complexes, and other industrial facilities. For example, a medium-size integrated crude oil refinery with aromatics up to 4,000 MM British Thermal Units per hour (Btu/hr) can be wasted to a network of air coolers extended along the crude oil and aromatics site. Some of the wasted heat can be reused to heat streams in refining sub-units of the crude oil refinery, thereby decreasing a quantity of heat that would otherwise need to be used to heat the streams. In this manner, a quantity of heat consumed by the crude oil refinery can decrease. In addition, a quantity of greenhouse gas (GHG) emission can also decrease. In some implementations, a reduction of about 34% in heating utility consumption and a reduction of about 20% in cooling utility consumption can be achieved without affecting an operational philosophy of the crude oil refinery.

The waste heat recovery and reuse techniques described here can be implemented in medium grade crude oil refining semi-conversion facilities and integrated medium grade crude oil refining semi-conversion oil refining and aromatics facilities. The implementations can result in energy efficient systems that can consume about 66% of the heating utility consumed by current state-of-the-art designs of existing and new crude oil refining facilities. The implementations can also result in decrease in pollution and in GHG emissions by about one-third relative to GHG emissions from current state-of-the-art designs of existing and new crude oil refining facilities.

In certain existing oil refining facilities, a stream in a plant (for example, a naphtha hydro-treating plant, a sour water stripper plant, or other plant) is heated using heat energy generated in a steam reboiler. In some implementations of the subject matter described here, the stream in the plant can be heated using waste heat carried by another stream in another plant (for example, a hydrocracking plant, a hydro-treating plant, a hydrogen plant, or other plant). By doing so, the heat energy generated in the steam reboiler can be decreased or eliminated. In other words, the steam reboiler need not be the only source of heat energy to heat the stream in the plant. The waste heat carried by the other stream in the other plant can either replace the heat energy generated in the steam reboiler or supplement the heat energy thereby decreasing a quantity of heat energy needed from the steam reboiler.

The subject matter described here can be implemented at different plants' specific operating modes and can be retrofitted without the need to change the network designs of existing heat exchanger designs in crude oil refineries. The minimum approach temperature used in the waste heat recovery and reuse processes can be as low as 3° C. In some implementations, higher minimum approach temperatures can be used in an initial phase at the expense of less waste heat/energy recovery, while relatively better energy saving is realized in a subsequent phase upon using the minimum approach temperature for the specific hot sources uses.

In sum, this disclosure describes several crude oil refinery-wide separation/distillation networks, configurations, and processing schemes for increasing energy efficiency of heating/cooling utilities. The increase in energy efficiency is realized by reusing all or part of waste heat, for example, low grade waste heat, carried by multiple, scattered low grade energy quality process streams.

Examples of Crude Oil Refinery Plants

1. Hydrogen Plant

Hydrogen is generally used in refineries for sulfur removal and quality improvement of hydrocarbon products. As sulfur restrictions on gasoline and diesel become stringent, the refining demand for hydrogen continues to grow. Two process schemes are employed in on-purpose hydrogen generation plants—conventional process and pressure swing adsorption (PSA) based process. Hydrogen production can include hydro-desulfurization, steam reforming, shift conversion and purification. The conventional process produces a medium-purity hydrogen, whereas the PSA-based process recovers and purifies the hydrogen to high purities, for example, purities greater than 99.9%.

2. Aromatics Complex

A typical aromatics complex includes a combination of process units for the production of basic petrochemical intermediates of benzene, toluene and xylenes (BTX) using the catalytic reforming of naphtha using continuous catalytic reformer (CCR) technology.

3. Gas Separation Plant

A gas separation Plant includes a de-ethanizer and a de-propanizer, which are distillation columns used to isolate ethane and propane, respectively, in natural gas liquids (NGL) and light ends fractionation in gas plants and refineries. The de-ethanizer removes ethane from a mixture of propane, butane and other heavier components. An output of the de-ethanizer is fed to a de-propanizer to separate propane from the mixture.

4. Amine Regeneration Plant

Hydrogen sulfide and carbon dioxide are the most common contaminants present in natural gas and are present in relatively larger quantities than other contaminants which can adversely impact the natural gas processing facility if not removed. Amine is used in an acid gas absorber and regenerator to sweeten sour gases in a chemical process in which a weak base (for example, the amine) reacts with weak acids such as hydrogen sulfide and carbon dioxide to form a weak salt.

5. Hydrocracking Plant

Hydrocracking is a two-stage process combining catalytic cracking and hydrogenation. In this process heavy feedstocks are cracked in the presence of hydrogen to produce more desirable products. The process employs high pressure, high temperature, a catalyst, and hydrogen. Hydrocracking is used for feedstocks that are difficult to process by either catalytic cracking or reforming, since these feedstocks are characterized usually by high polycyclic aromatic content or high concentrations of the two principal catalyst poisons, sulfur and nitrogen compounds (or combinations of them).

The hydrocracking process depends on the nature of the feedstock and the relative rates of the two competing reactions, hydrogenation and cracking. Heavy aromatic feedstock is converted into lighter products under a wide range of high pressures and high temperatures in the presence of hydrogen and special catalysts. When the feedstock has a high paraffinic content, hydrogen prevents the formation of polycyclic aromatic compounds. Hydrogen also reduces tar formation and prevents buildup of coke on the catalyst. Hydrogenation additionally converts sulfur and nitrogen compounds present in the feedstock to hydrogen sulfide and ammonia. Hydrocracking produces iso-butane for alkylation feedstock, and also performs isomerization for pour-point control and smoke-point control, both of which are important in high-quality jet fuel.

6. Diesel Hydrotreating Plant

Hydrotreating is a refinery process for reducing sulfur, nitrogen and aromatics while enhancing cetane number, density and smoke point. Hydrotreating assists the refining industry's efforts to meet the global trend for stringent clean fuels specifications, the growing demand for transportation fuels and the shift toward diesel. In this process, fresh feed is heated and mixed with hydrogen. Reactor effluent exchanges heat with the combined feed and heats recycle gas and stripper charge. Sulphide (for example, ammonium bisulphide and hydrogen sulphide) is then removed from the feed.

7. Sour Water Stripper Utility Plant (SWSUP)

The SWSUP receives sour water streams from acid gas removal, sulfur recovery, and flare units, and the sour gas stripped and released from the soot water flash vessel. The SWSUP strips the sour components, primarily carbon dioxide ($CO_2$), hydrogen sulfide ($H_2S$) and ammonia ($NH_3$), from the sour water stream.

8. Sulfur Recovery Plant

Sulfur removal facilities in refineries operate to regulate the discharge of sulfur compounds to the atmosphere to meet environmental regulations. In a sulfur recovery plant, combustion products that include sulfur can be processed, for example, by heating, cooling with condensers, using sulfur conversion catalyst, and by other processing techniques. One technique is to use amines to extract the sulfur and other acid gas compounds.

9. Naphtha Hydrotreating Plant and Continuous Catalytic Reformer Plants

A Naphtha Hydrotreater (NHT) produces 101 Research Octane Number (RON) reformate, with a maximum 4.0 psi (pounds per square inch) Reid Vapor Pressure (RVP), as a blending stock in the gasoline pool. It usually has the flexibility to process blends of Naphtha from the Crude Unit, Gas Condensate Splitter, Hydrocracker, Light Straight-Run Naphtha (LSRN) and Visbreaker Plants. The NHT processes naphtha to produce desulfurized feed for the CCR platformer and gasoline blending.

Heat Exchangers

In the configurations described in this disclosure, heat exchangers are used to transfer heat from one medium (for example, a stream flowing through a plant in a crude oil refining facility, a buffer fluid or other medium) to another medium (for example, a buffer fluid or different stream flowing through a plant in the crude oil facility). Heat exchangers are devices which transfer (exchange) heat typically from a hotter fluid stream to a relatively less hotter fluid stream. Heat exchangers can be used in heating and cooling applications, for example, in refrigerators, air conditions or other cooling applications. Heat exchangers can be distinguished from one another based on the direction in which liquids flow. For example, heat exchangers can be parallel-flow, cross-flow or counter-current. In parallel-flow heat exchangers, both fluid involved move in the same direction, entering and exiting the heat exchanger side-by-side. In cross-flow heat exchangers, the fluid path runs perpendicular to one another. In counter-current heat exchangers, the fluid paths flow in opposite directions, with one fluid exiting whether the other fluid enters. Counter-current heat exchangers are sometimes more effective than the other types of heat exchangers.

In addition to classifying heat exchangers based on fluid direction, heat exchangers can also be classified based on their construction. Some heat exchangers are constructed of multiple tubes. Some heat exchangers include plates with room for fluid to flow in between. Some heat exchangers enable heat exchange from liquid to liquid, while some heat exchangers enable heat exchange using other media.

Heat exchangers in crude oil refining and petrochemical facilities are often shell and tube type heat exchangers which include multiple tubes through which liquid flows. The tubes are divided into two sets—the first set contains the liquid to be heated or cooled; the second set contains the liquid responsible for triggering the heat exchange, that is, the fluid that either removes heat from the first set of tubes by absorbing and transmitting the heat away or warms the first set by transmitting its own heat to the liquid inside. When designing this type of exchanger, care must be taken in determining the correct tube wall thickness as well as tube diameter, to allow optimum heat exchange. In terms of flow, shell and tube heat exchangers can assume any of three flow path patterns.

Heat exchangers in crude oil refining and petrochemical facilities can also be plate and frame type heat exchangers. Plate heat exchangers include thin plates joined together with a small amount of space in between, often maintained by a rubber gasket. The surface area is large, and the corners of each rectangular plate feature an opening through which fluid can flow between plates, extracting heat from the plates as it flows. The fluid channels themselves alternate hot and cold liquids, meaning that the heat exchangers can effectively cool as well as heat fluid. Because plate heat exchangers have large surface area, they can sometimes be more effective than shell and tube heat exchangers.

Other types of heat exchangers can include regenerative heat exchangers and adiabatic wheel heat exchangers. In a regenerative heat exchanger, the same fluid is passed along both sides of the exchanger, which can be either a plate heat exchanger or a shell and tube heat exchanger. Because the fluid can get very hot, the exiting fluid is used to warm the incoming fluid, maintaining a near constant temperature. Energy is saved in a regenerative heat exchanger because the process is cyclical, with almost all relative heat being transferred from the exiting fluid to the incoming fluid. To maintain a constant temperature, a small quantity of extra energy is needed to raise and lower the overall fluid temperature. In the adiabatic wheel heat exchanger, an intermediate liquid is used to store heat, which is then transferred to the opposite side of the heat exchanger. An adiabatic wheel consists of a large wheel with threats that rotate through the liquids—both hot and cold—to extract or transfer heat. The heat exchangers described in this disclosure can include any one of the heat exchangers described earlier, other heat exchangers, or combinations of them.

Each heat exchanger in each configuration can be associated with a respective thermal duty (or heat duty). The thermal duty of a heat exchanger can be defined as an amount of heat that can be transferred by the heat exchanger from the hot stream to the cold stream. The amount of heat can be calculated from the conditions and thermal properties of both the hot and cold streams. From the hot stream point of view, the thermal duty of the heat exchanger is the product of the hot stream flow rate, the hot stream specific heat, and a difference in temperature between the hot stream inlet temperature to the heat exchanger and the hot stream outlet temperature from the heat exchanger. From the cold stream point of view, the thermal duty of the heat exchanger is the product of the cold stream flow rate, the cold stream specific heat and a difference in temperature between the cold stream outlet from the heat exchanger and the cold stream inlet temperature from the heat exchanger. In several applications, the two quantities can be considered equal assuming no heat loss to the environment for these units, particularly, where the units are well insulated. The thermal duty of a heat exchanger can be measured in watts (W), megawatts (MW), millions of British Thermal Units per hour (Btu/hr), or millions of kilocalories per hour (Kcal/h). In the configurations described here, the thermal duties of the heat exchangers are provided as being "about X MW," where "X" represents a numerical thermal duty value. The numerical thermal duty value is not absolute. That is, the actual thermal duty of a heat exchanger can be approximately equal to X, greater than X or less than X.

Configurations in which heat exchangers are described as being in series can have multiple implementations. In some implementations, the heat exchangers can be arranged in series in one order (for example, a first heat exchanger, a second heat exchanger and a third heat exchanger in that order) while in other implementations, the heat exchangers can be arranged in series in a different order (for example, a third heat exchanger, a first heat exchanger and a second heat exchanger in that order). In other words, a first heat exchanger described as being in series with and downstream of a second heat exchanger in one implementation can be in series with and upstream of the second heat exchanger in a second, different implementation.

Flow Control System

In each of the configurations described later, process streams (also called "streams") are flowed within each plant in a crude oil refining facility and between plants in the crude oil refining facility. The process streams can be flowed using one or more flow control systems implemented throughout the crude oil refining facility. A flow control system can include one or more flow pumps to pump the process streams, one or more flow pipes through which the process streams are flowed and one or more valves to regulate the flow of streams through the pipes.

In some implementations, a flow control system can be operated manually. For example, an operator can set a flow rate for each pump and set valve open or close positions to regulate the flow of the process streams through the pipes in the flow control system. Once the operator has set the flow rates and the valve open or close positions for all flow control systems distributed across the crude oil refining facility, the flow control system can flow the streams within a plant or between plants under constant flow conditions, for example, constant volumetric rate or other flow conditions. To change the flow conditions, the operator can manually operate the flow control system, for example, by changing the pump flow rate or the valve open or close position.

In some implementations, a flow control system can be operated automatically. For example, the flow control system can be connected to a computer system to operate the flow control system. The computer system can include a computer-readable medium storing instructions (such as flow control instructions and other instructions) executable by one or more processors to perform operations (such as flow control operations). An operator can set the flow rates and the valve open or close positions for all flow control systems distributed across the crude oil refining facility using the computer system. In such implementations, the operator can manually change the flow conditions by providing inputs through the computer system. Also, in such implementations, the computer system can automatically (that is, without manual intervention) control one or more of the flow control systems, for example, using feedback systems implemented in one or more plants and connected to the computer system. For example, a sensor (such as a pressure sensor, temperature sensor or other sensor) can be connected to a pipe through which a process stream flows. The sensor can monitor and provide a flow condition (such as a pressure, temperature, or other flow condition) of the process stream to the computer system. In response to the flow condition exceeding a threshold (such as a threshold pressure value, a threshold temperature value, or other threshold value), the computer system can automatically perform operations. For example, if the pressure or temperature in the pipe exceeds the threshold pressure value or the threshold temperature value, respectively, the computer system can provide a signal to the pump to decrease a flow rate, a signal to open a valve to relieve the pressure, a signal to shut down process stream flow, or other signals.

This disclosure describes advanced energy efficient configuration and related processing schemes for integrated medium grade crude oil semi-conversion refining facility and aromatics complex.

In some implementations, a semi-conversion medium grade crude oil refining facility includes almost all plants in the refining facility including, for example, an aromatics complex and a hydrocracking plant. This disclosure describes a waste heat recovery and reuse network for such a refining facility. As described later, waste heat can be recovered from multiple plants in the crude oil refining facility including a hydrocracking plant. Such a refinery typically consumes several hundred megawatts of energy in heating utilities. Implementing the configurations described here can not only reduce energy consumption but also reduce energy-based greenhouse gas (GHG) emissions. In particular, this disclosure describes a method implemented in a crude oil refining facility to heat multiple first streams in multiple first plants of a crude oil refining facility using multiple second streams in multiple second plants in the crude oil refining facility. Several configurations of process schemes for doing so are described later with reference to the following figures.

Scheme A

Figure 1B:
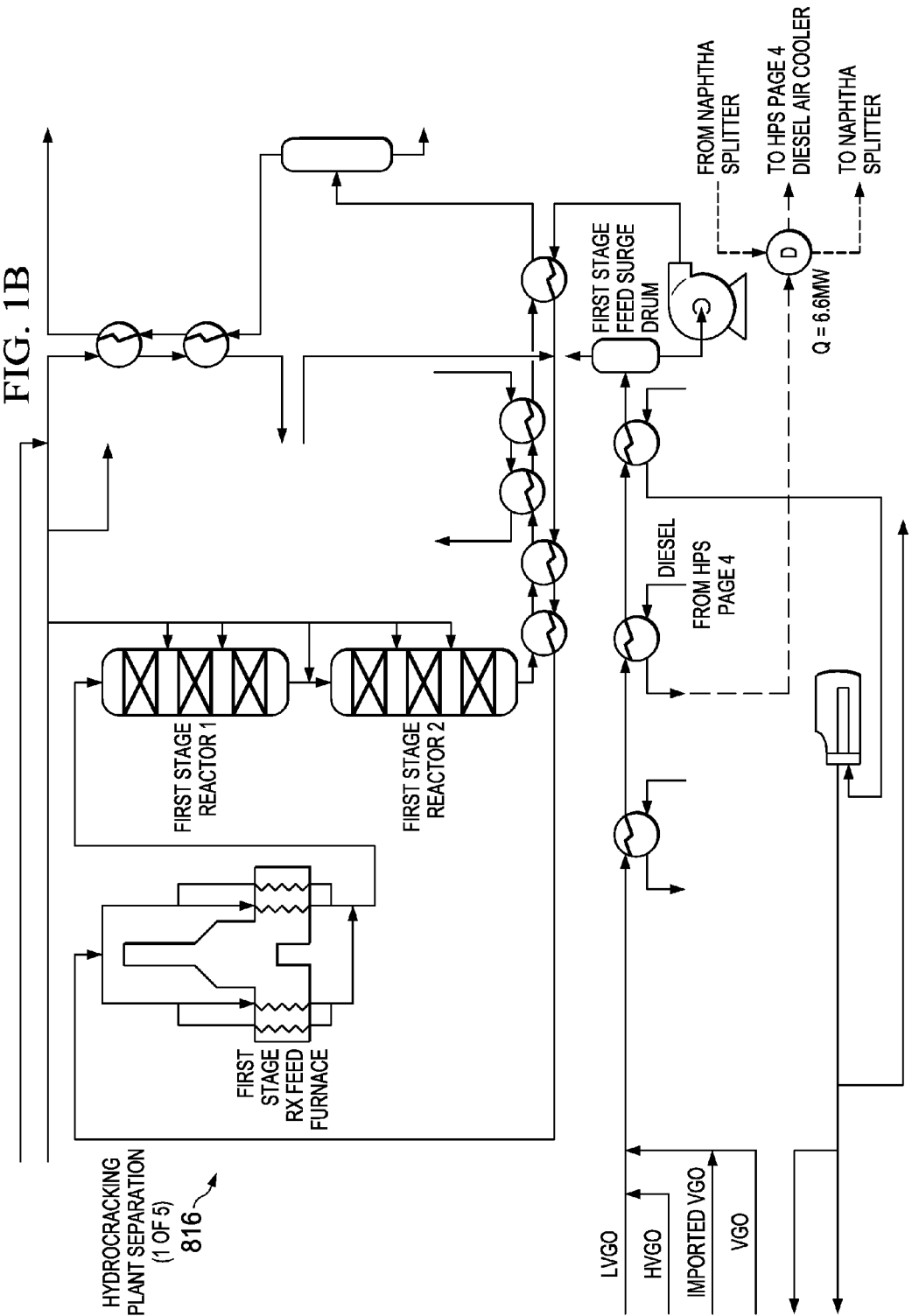
Figure 1C:
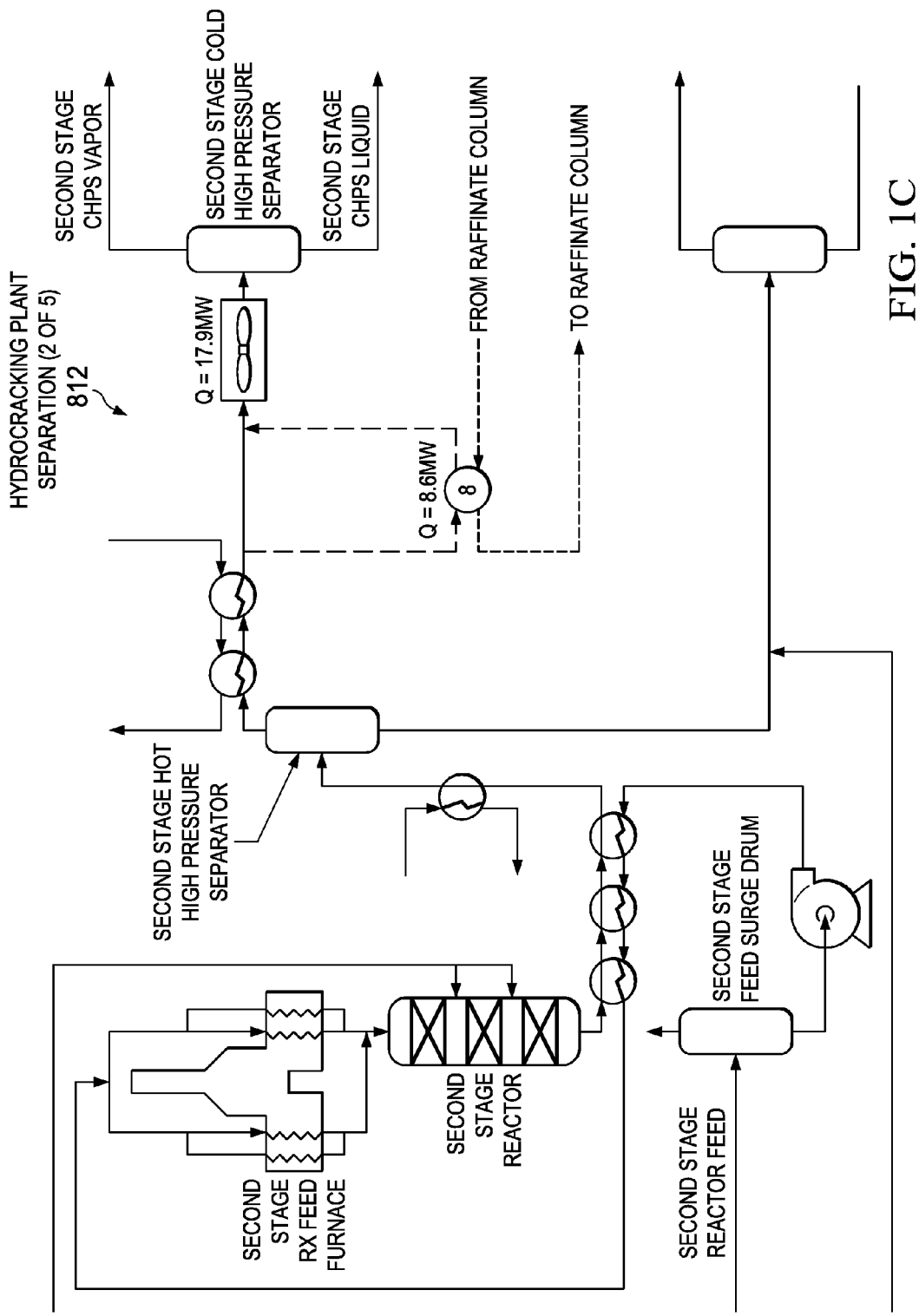
Figure 1D:
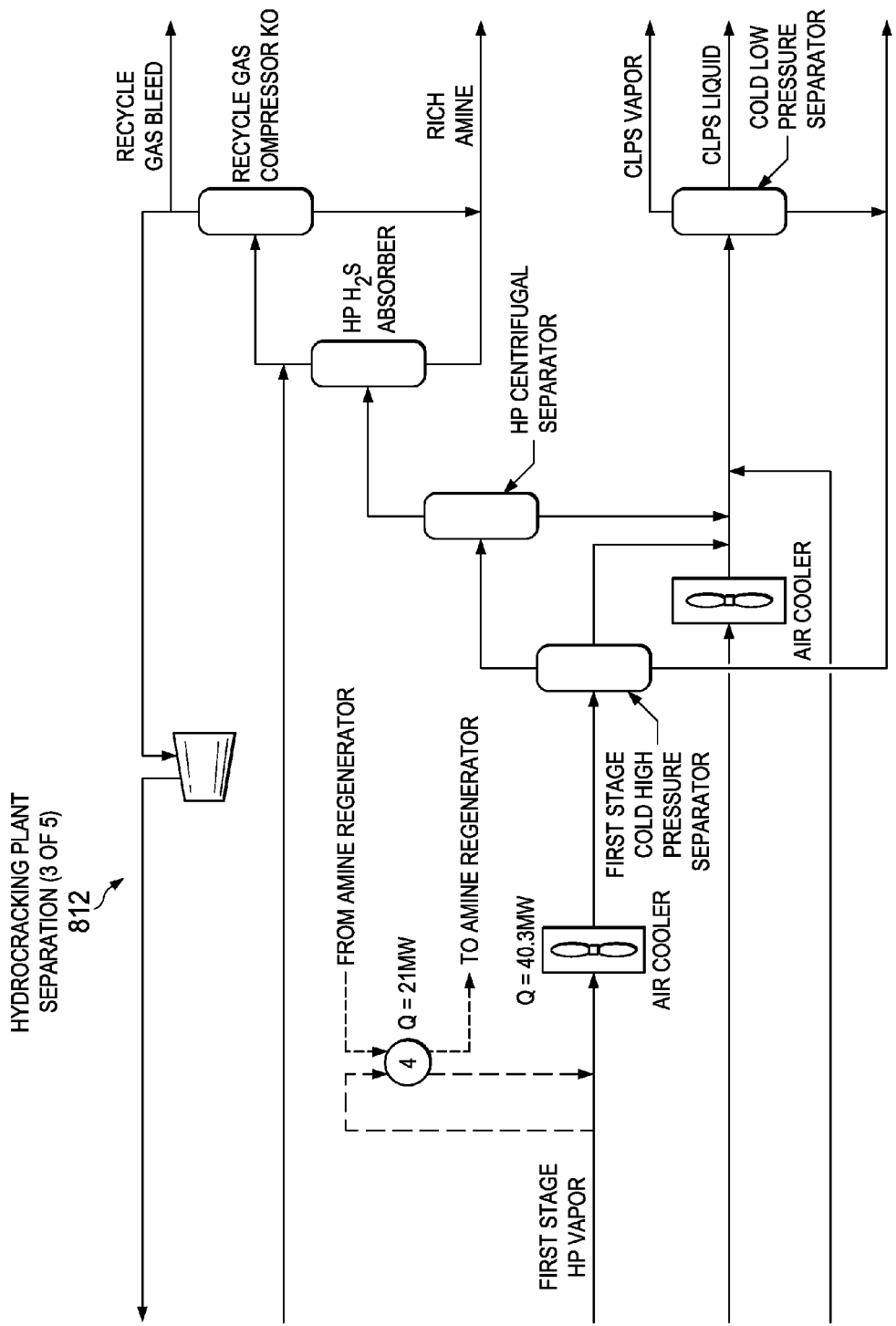
Figures 1, 1E:
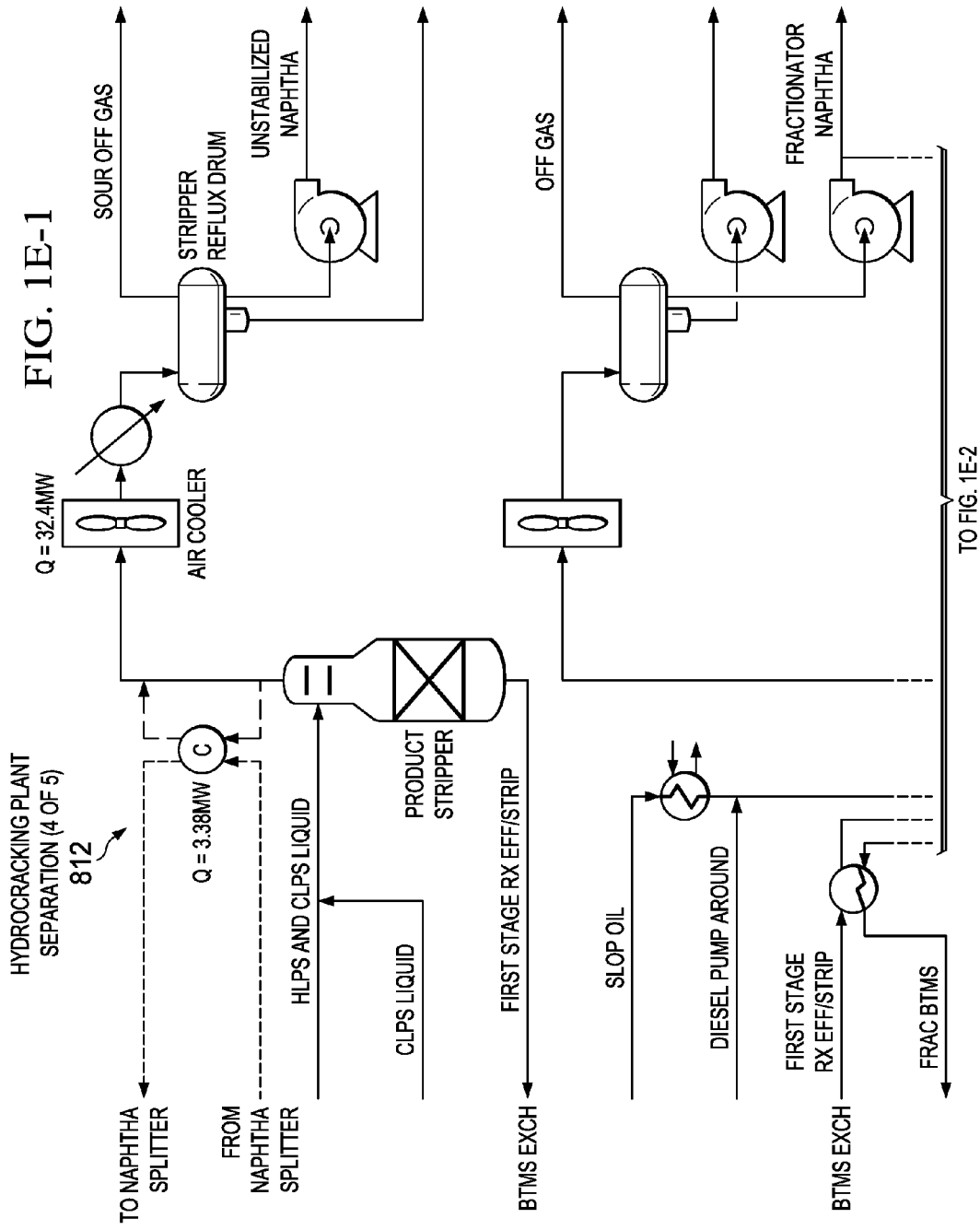
Figures 1, 1E, 2:
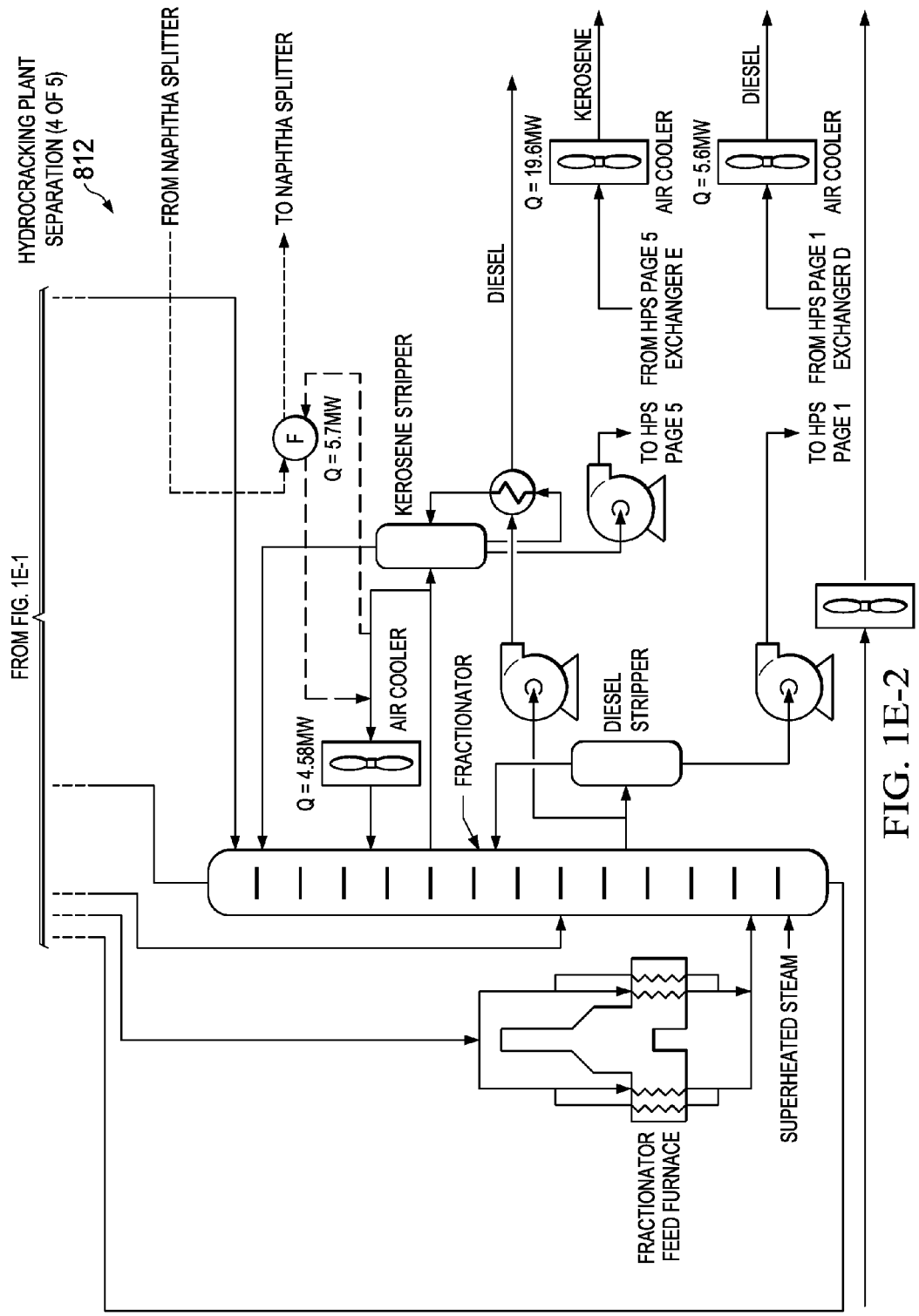
Figure 1F:
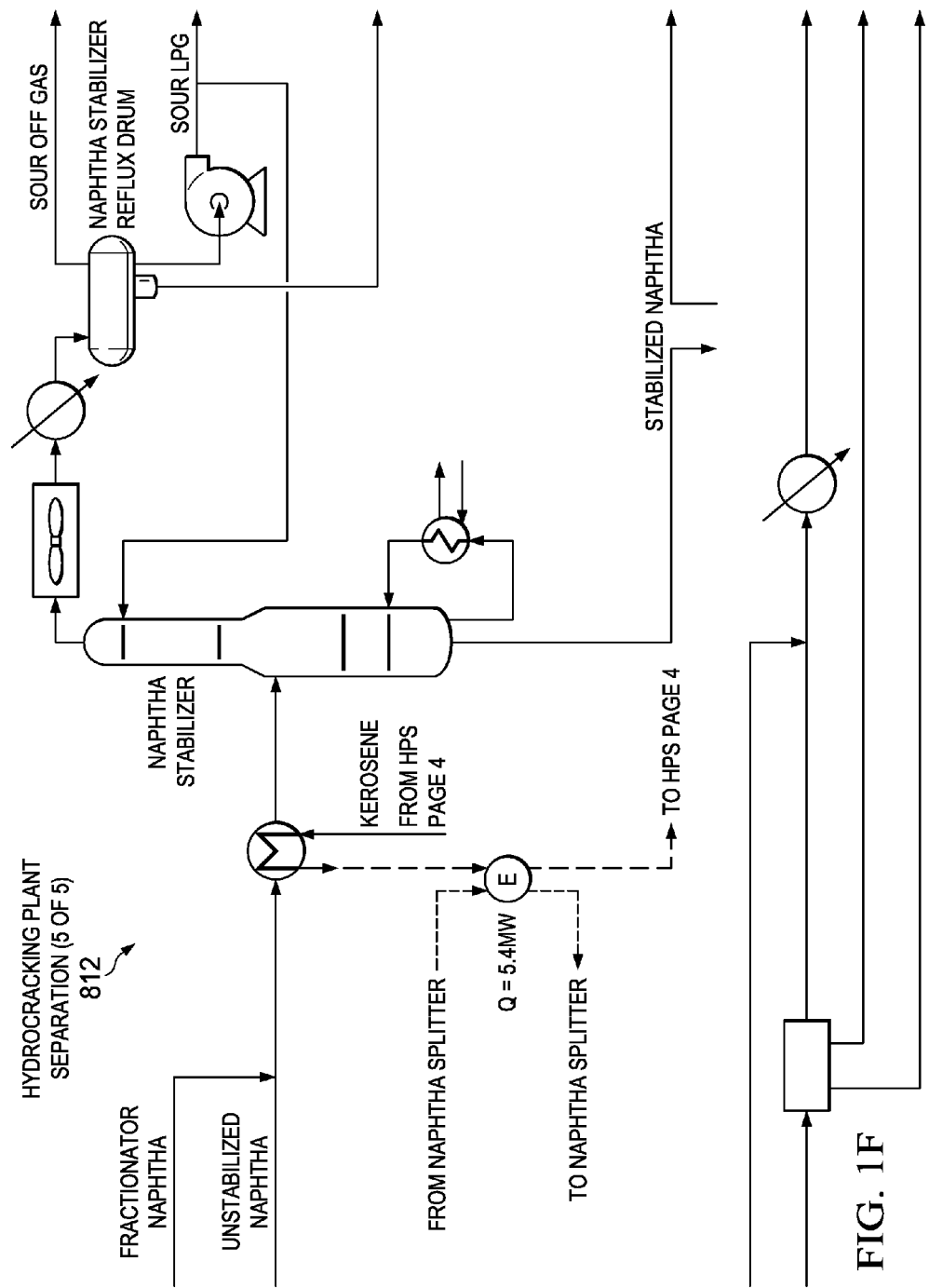
Figure 1G:
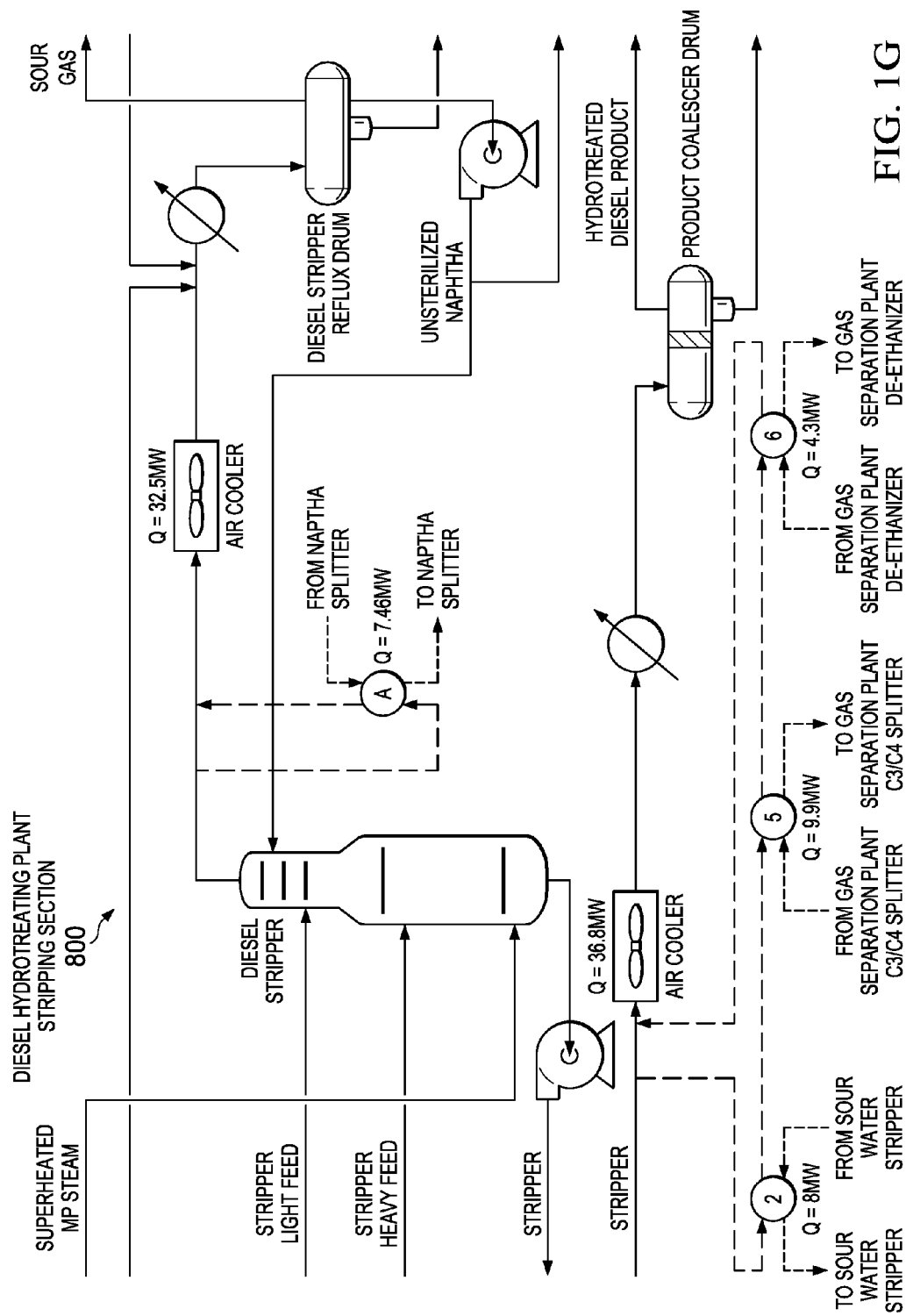
Figure 1H:
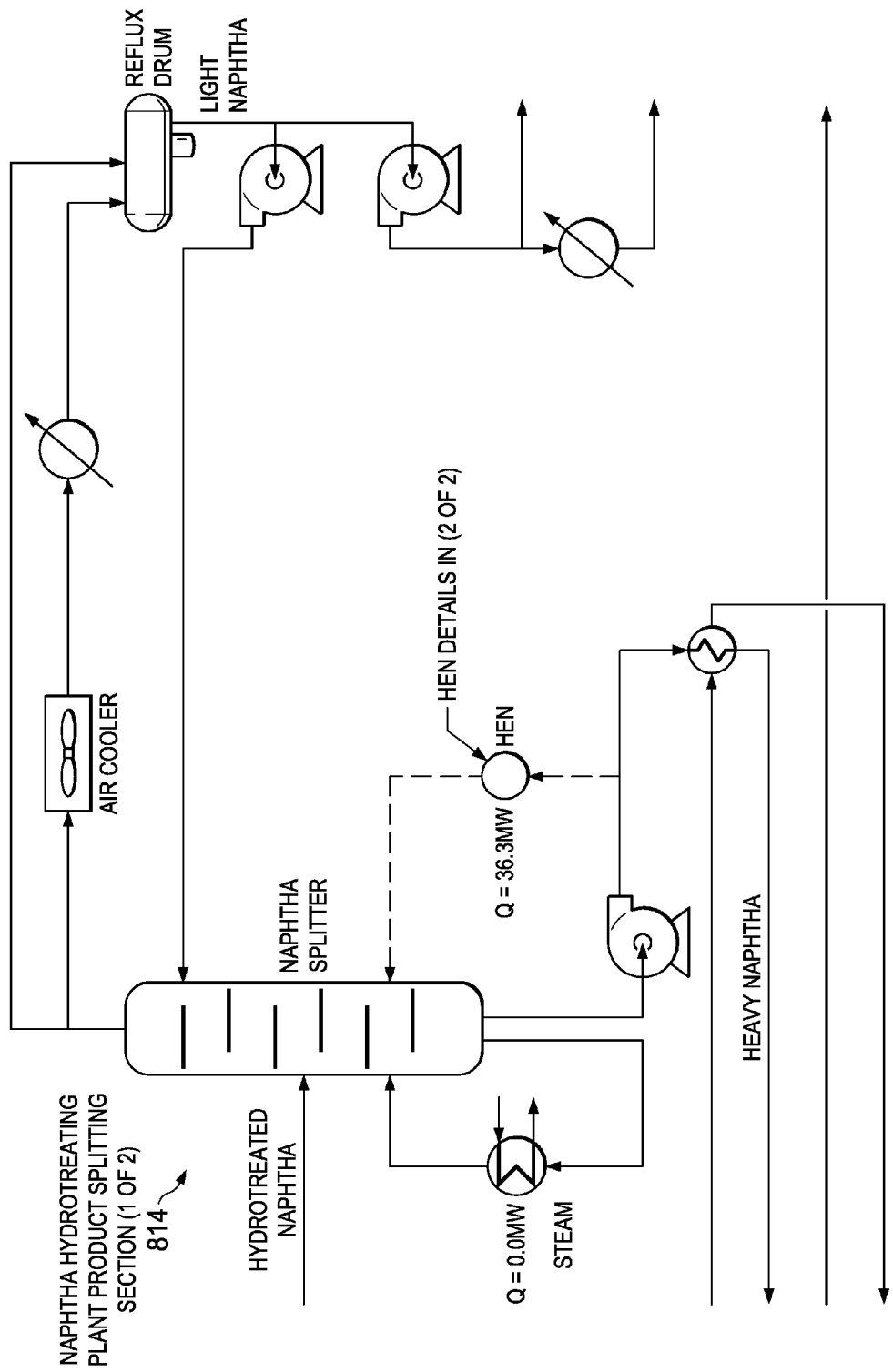
Figure 1I:
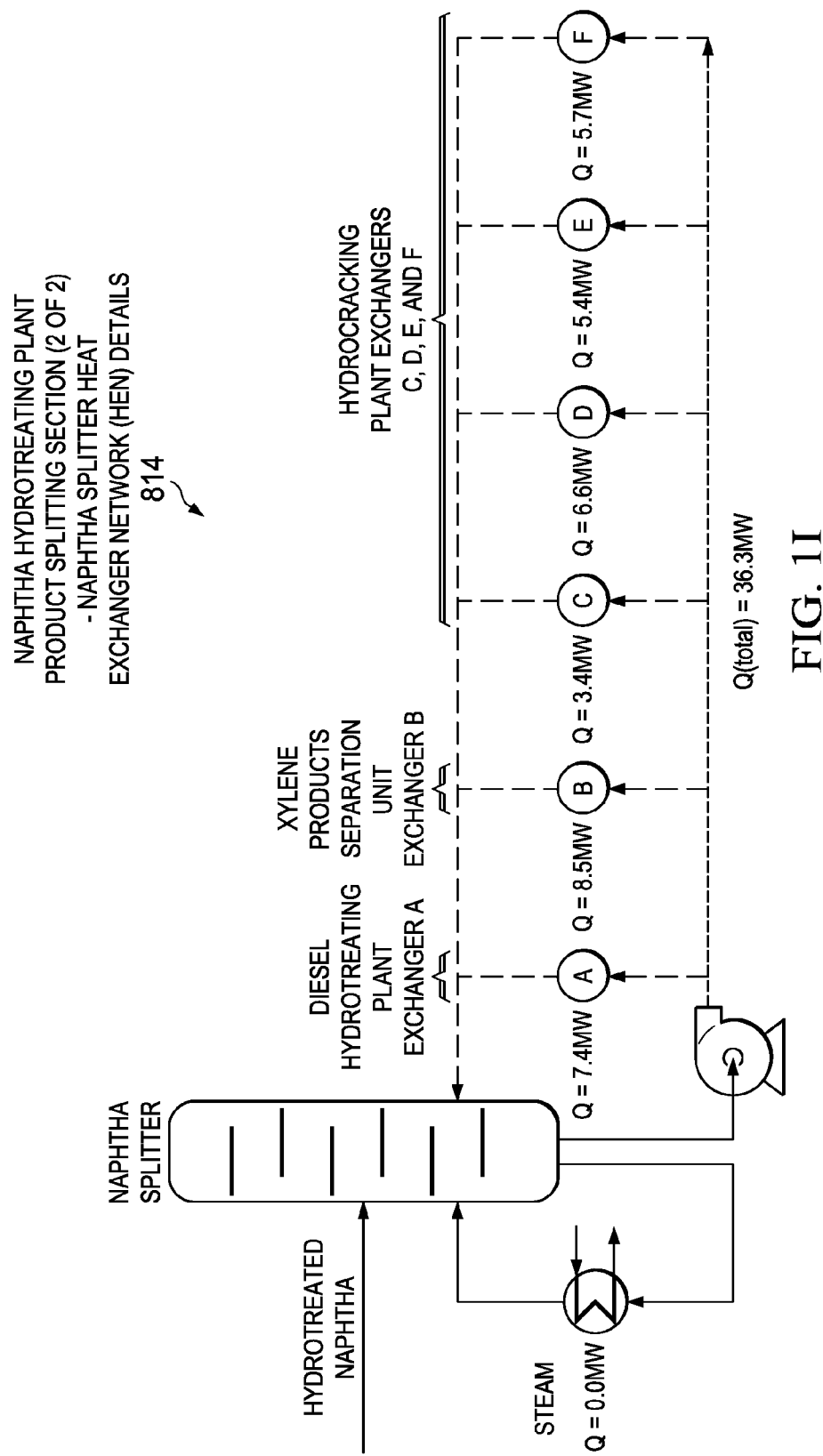
Figure 1J:
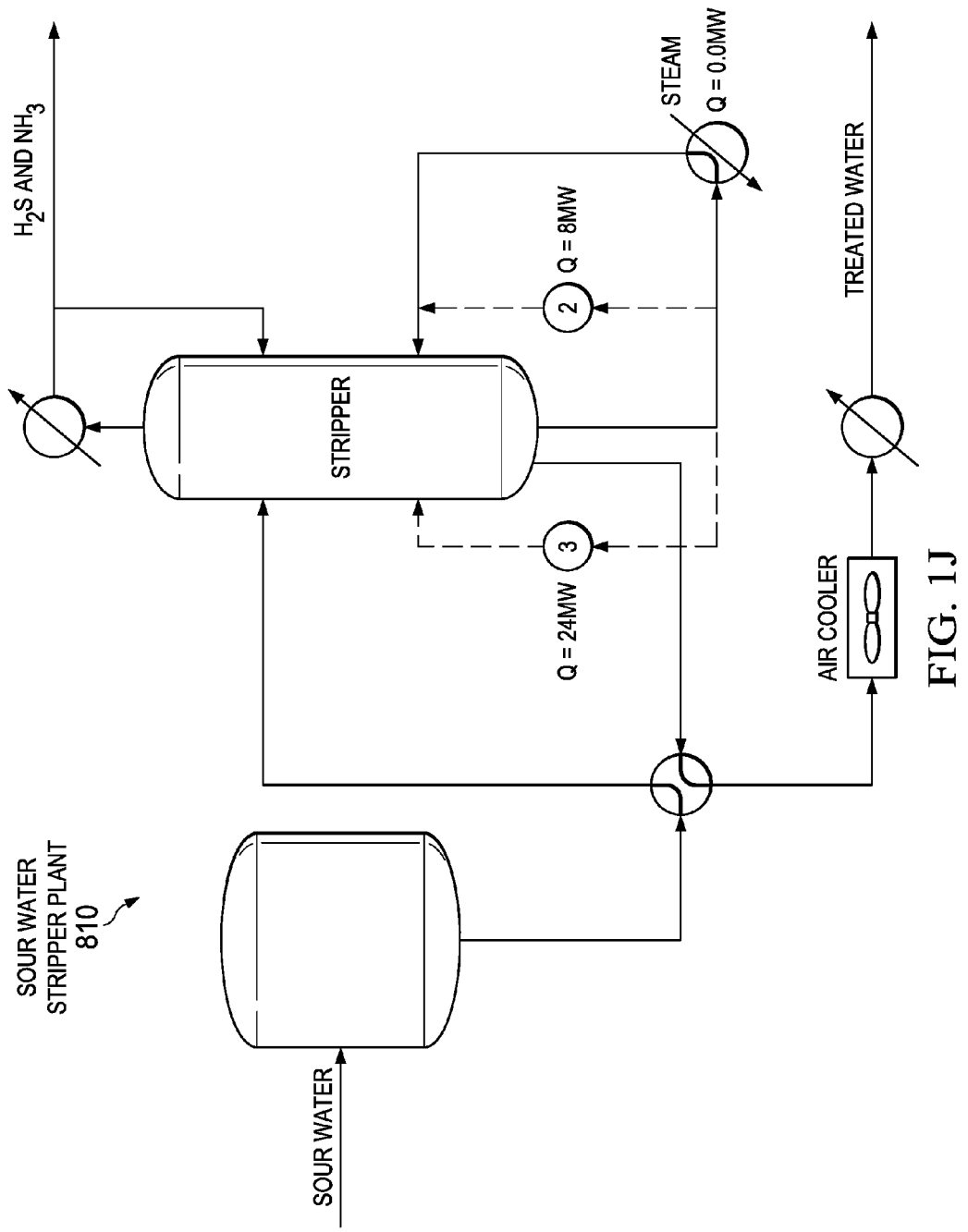
Figure 1K:
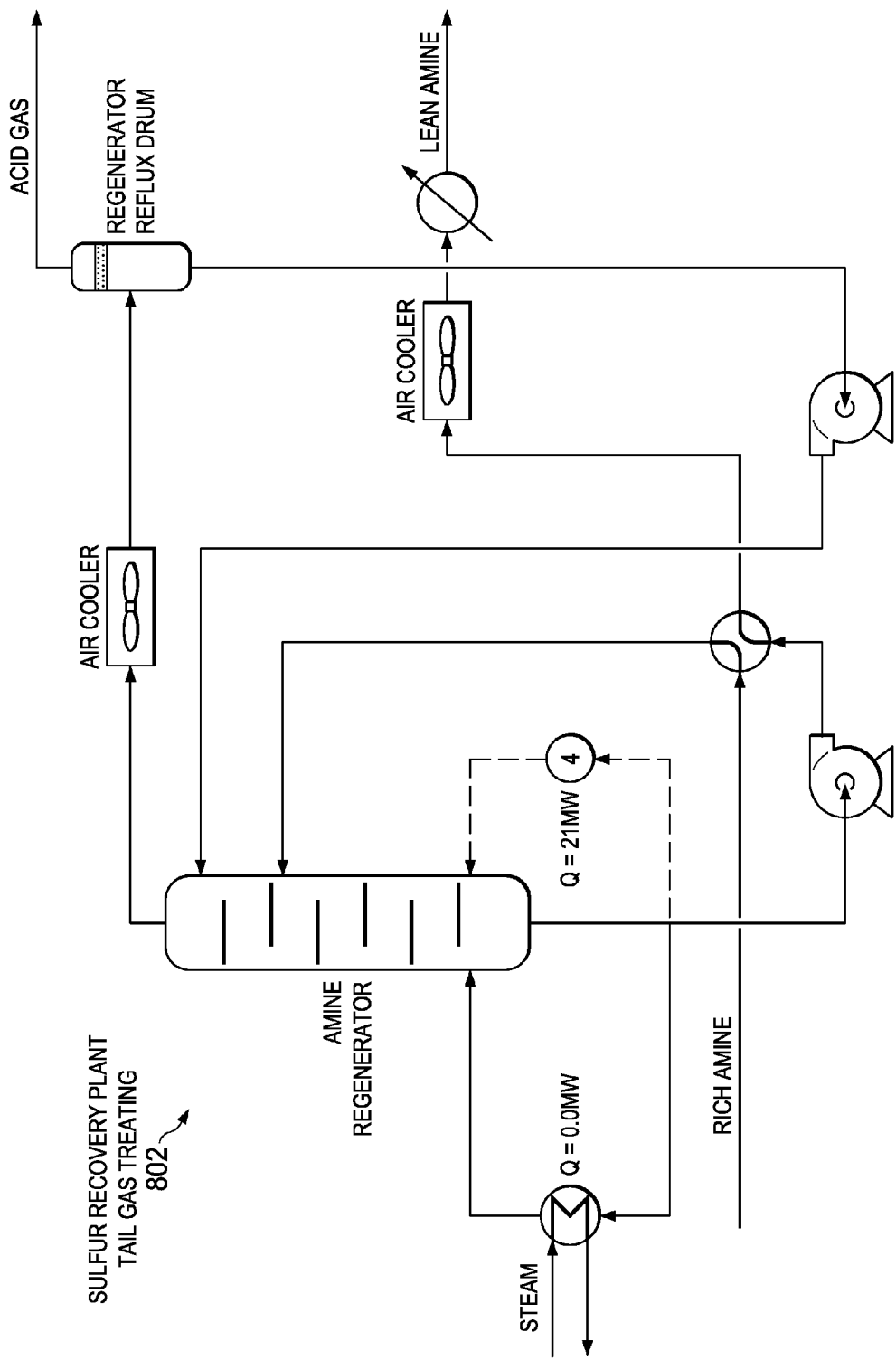
Figure 1L:
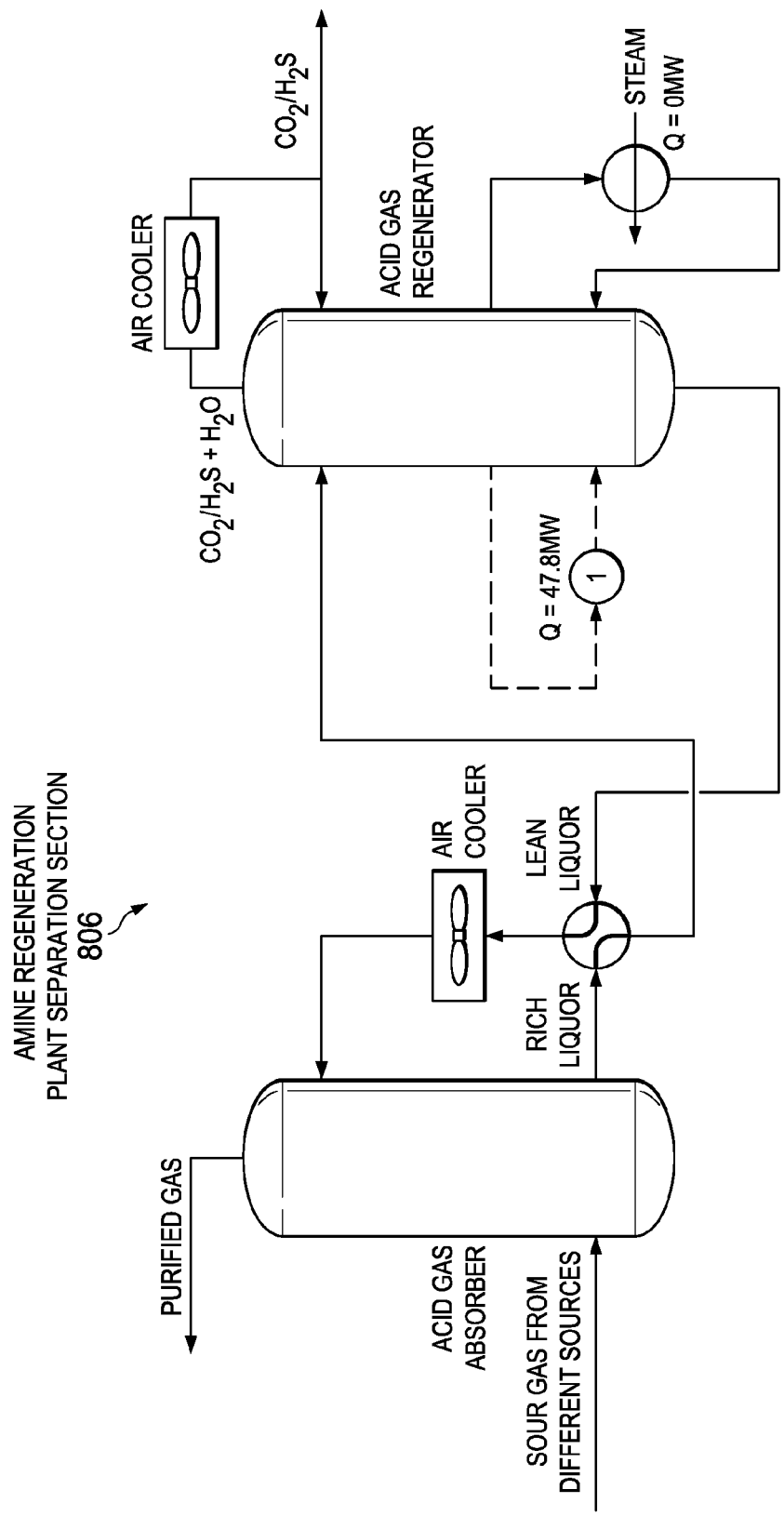
Figure 1M:
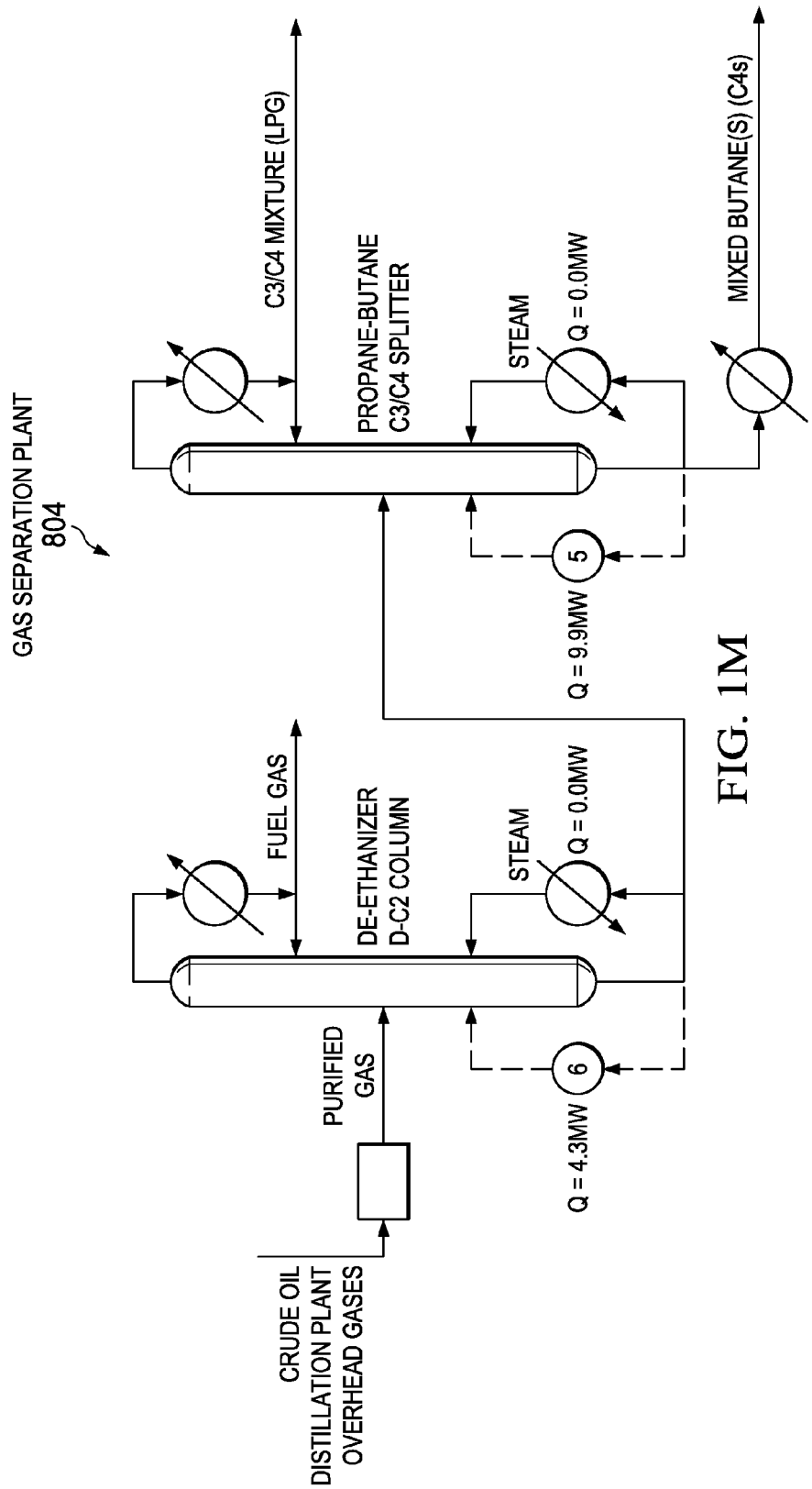
Figure 1N:
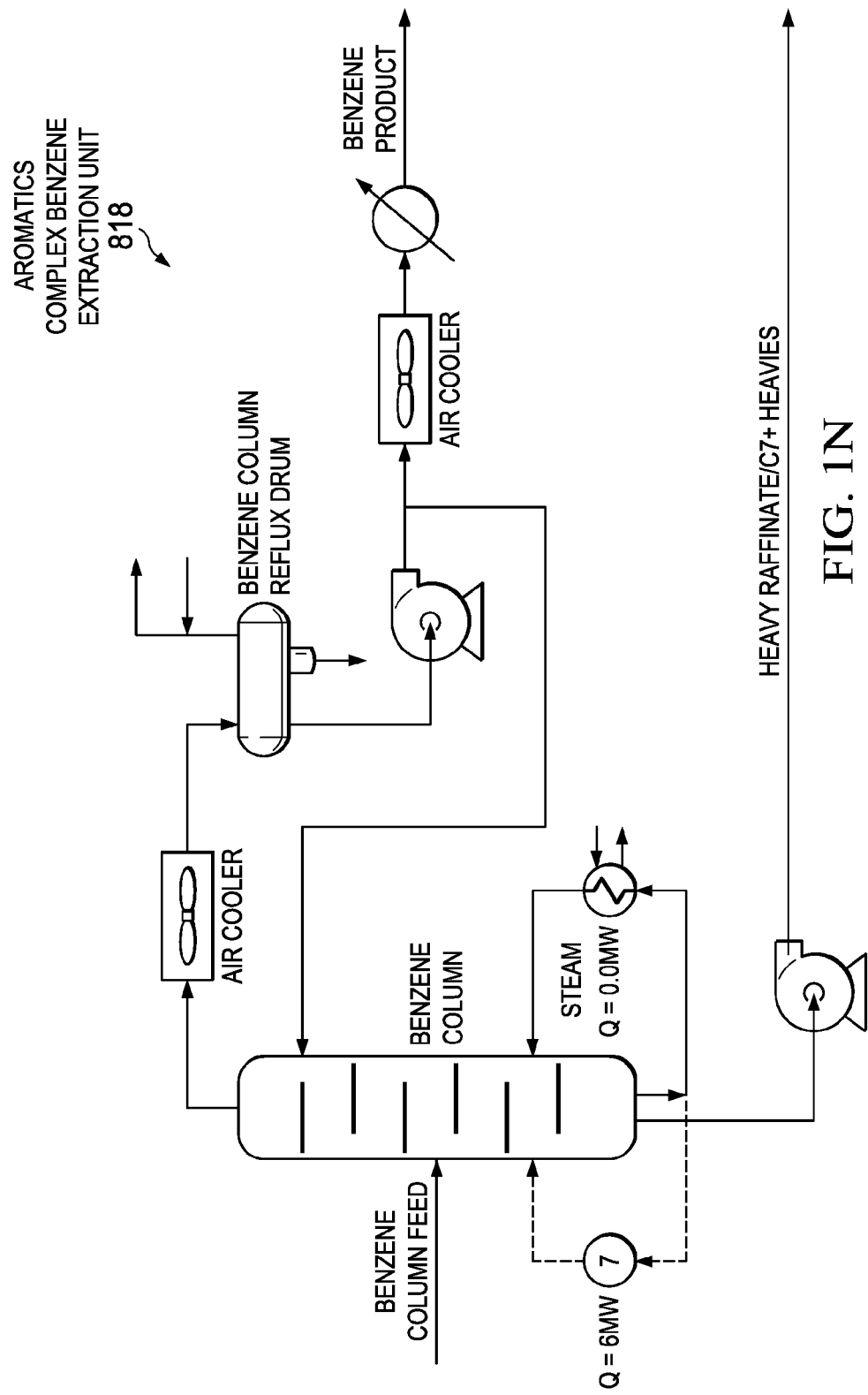
Figure 1O:
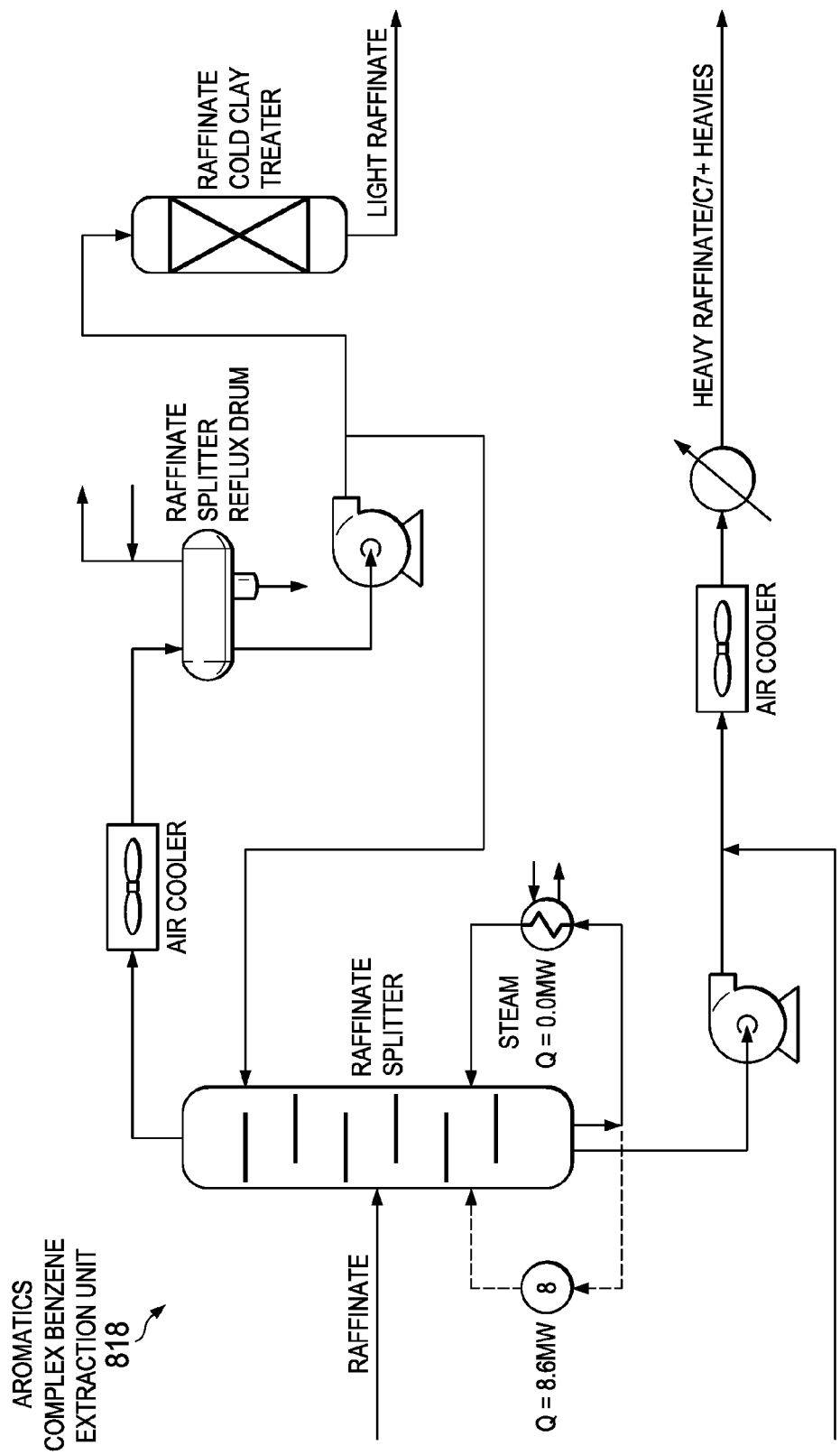

FIGS. 1A-1O illustrate configurations and related scheme details for thermally integrating different refining plants in the crude oil refining facility. The thermal integration described in these configurations and illustrated in FIGS. 1A-1O can reduce the crude oil refining facility's energy consumption (for example, heating and cooling utilities). For example, a reduction in energy consumption by about 166 MW, for example, 166 MW, can translate to at least about 25%, for example, 25.5%, of the energy consumption in the crude oil refining facility. In certain schemes, a process stream from one refining plant can be used to directly heat another process stream from another, different refining plant. In certain configurations, heat exchange between process streams can be implemented using an intermediate buffer fluid, for example, water, oil, or other buffer fluid. In other schemes, the two techniques are used in combination with one another.

In some implementations, multiple first streams in the multiple first plants can be directly heated using multiple second streams in the multiple second plants. In some implementations, the multiple first plants can include an amine regeneration plant, an aromatics complex sub-unit including a benzene extraction unit, a naphtha hydro-treating plant, a sour water stripper plant, a sulfur recovery plant, and a gas separation plant. The multiple second streams include a raffinate column overheads, an extract column overheads, a diesel product, diesel stripper bottom, a feed stream to a first stage reaction cold high pressure separator, a feed stream to the second stage reaction cold high pressure separator, diesel stripper overhead, a product stripper overhead, a kerosene product and a kerosene pumparound streams. The multiple second plants can include another aromatics complex sub-unit including an aromatics complex xylene products separation unit (sometimes known as xylene separation unit), a hydrocracking plant, and a diesel hydrotreating plant. The multiple first streams include an acid gas regenerator bottoms, a sour water stripper bottoms, an amine regenerator bottoms, a C3/C4 splitter column bottoms, a de-ethanizer column bottoms, a benzene column bottoms, a raffinate splitter bottoms and a naphtha splitter bottoms streams. In some implementations, one of the first plant streams from one of the first plants is directly heated by multiple second streams from three of the second plants. In some implementations, one of the first plant streams from one of the first plants is directly heated by multiple second streams from two of the second plants.

FIG. 1A shows an aromatics complex xylene products separation unit 820 in a crude oil refinery facility. The raffinate overheads column stream can be flowed in the plant as a single stream and split into multiple streams or it can be flowed into the plant as multiple streams to facilitate heat recovery. A first raffinate column overhead streams can directly heat an acid gas regenerator bottoms stream in a first heat exchanger with a thermal duty that can range between about 45 MW and 55 MW (for example, 47.8 MW). The transfer of heat directly to another process stream captures heat that would have otherwise been discharged to the environment.

FIG. 1G shows a diesel hydrotreating plant 800 in a crude oil refinery facility. FIG. 1J shows a sour water stripper plant 810 in a crude oil refinery facility. The sour water stripper bottoms stream can be flowed in the plant as a single stream and split into multiple streams or it can be flowed into the plant as multiple streams to facilitate heat recovery. As shown in FIG. 1G, a diesel stripper bottoms stream can directly heat a first sour water stripper bottoms stream in a second heat exchanger with a thermal duty that can range between about 5 MW and 15 MW (for example, 8 MW). The transfer of heat directly to another process stream captures heat that would have otherwise been discharged to the environment. In this instance, the diesel stripper bottoms stream exiting the second heat exchanger is flowed to the fifth heat exchanger as described later.

As shown in FIG. 1A, an extract column overheads stream can directly heat a second sour water stripper bottoms stream in a third heat exchanger with a thermal duty that can range between about 20 MW and 30 MW (for example, 24 MW). The transfer of heat directly to another process stream captures heat that would have otherwise been discharged to the environment. The extract column overhead stream is returned to the xylene separation unit 820 for further processing.

As shown in FIG. 1J, the steam heat input for the sour water stripper can be 0 MW because the alternative flow path disclosed in this configuration may satisfy the entire heat load for the operation of the sour water stripper. In an alternative embodiment, the steam heat input for the sour water stripper can be reduced because the alternative flow path disclosed in this configuration may partially satisfy the heat load for the operation of the sour water stripper.

FIGS. 1B-1F show a hydrocracking plant 816 in a crude oil refinery facility. Specifically, FIG. 1D shows a feed stream to a first stage reaction cold high pressure separator in the hydrocracking plant 812 can directly heat an amine regenerator bottom stream in a fourth heat exchanger with a thermal duty that can range between about 15 MW and 25 MW (for example, 21 MW). The transfer of heat directly to another process stream captures heat that would have otherwise been discharged to the environment. The feed stream to the first stage reaction cold high pressure separator is returned to the hydrocracking plant for further processing.

FIG. 1K shows a sulfur recovery plant 802 in a crude oil refinery facility. The steam heat input for the amine regenerator can be 0 MW because the alternative flow path disclosed in this configuration may satisfy the entire heat load for the operation of the amine regenerator. In an alternative embodiment, the steam heat input for the amine regenerator can be reduced because the alternative flow path disclosed in this configuration may partially satisfy the heat load for the operation of the amine regenerator.

As shown in FIG. 1G, the diesel stripper bottom stream in can directly heat a C3/C4 splitter column bottom stream in a fifth heat exchanger with a thermal duty that can range between about 5 MW and 15 MW (for example, 9.9 MW). The transfer of heat directly to another process stream captures heat that would have otherwise been discharged to the environment. The diesel stripper bottom stream exiting the fifth heat exchanger is flowed to the sixth heat exchanger as described later.

FIG. 1M shows a gas separations plant 804 in a crude oil refinery facility. The steam heat input for the C3/C4 splitter column can be 0 MW because the alternative flow path disclosed in this configuration may satisfy the entire heat load for the operation of the C3/C4 splitter column. In an alternative embodiment, the steam heat input for the C3/C4 splitter column can be reduced because the alternative flow path disclosed in this configuration may partially satisfy the heat load for the operation of the C3/C4 splitter column.

As shown in FIG. 1G, the diesel stripper bottom stream can directly heat a de-ethanizer column bottom stream in a sixth heat exchanger with a thermal duty that can range between about 1 MW and 10 MW (for example, 4.3 MW). The transfer of heat directly to another process stream captures heat that would have otherwise been discharged to the environment. The diesel stripper bottoms stream is returned to the diesel hydrotreating plant 800 for further processing.

As shown in FIG. 1M, the steam heat input for the de-ethanizer column can be 0 MW because the alternative flow path disclosed in this configuration may satisfy the entire heat load for the operation of the de-ethanizer column. In an alternative embodiment, the steam heat input for the de-ethanizer column can be reduced because the alternative flow path disclosed in this configuration may partially satisfy the heat load for the operation of the de-ethanizer column.

As shown in FIG. 1A, a second raffinate splitter overhead stream in can directly heat a benzene column bottoms stream in a seventh heat exchanger with a thermal duty that can range between about 1 MW and 10 MW (for example, 6 MW). The transfer of heat directly to another process stream captures heat that would have otherwise been discharged to the environment.

FIG. 1N shows an aromatics complex benzene extraction unit 818 in a crude oil refinery facility. The steam heat input for the benzene column can be 0 MW because the alternative flow path disclosed in this configuration may satisfy the entire heat load for the operation of the benzene column. In an alternative embodiment, the steam heat input for the benzene column can be reduced because the alternative flow path disclosed in this configuration may partially satisfy the heat load for the operation of the benzene column.

As shown in FIG. 1C, a feed stream to the second stage reaction cold high pressure separator can directly heat a raffinate splitter bottom stream in an eighth heat exchanger with a thermal duty that can range between about 5 MW and 15 MW (for example, 9 MW). The transfer of heat directly to another process stream captures heat that would have otherwise been discharged to the environment. The feed stream to the second stage reaction cold high pressure separator is returned to the hydrocracking plant 812 for further processing.

FIG. 1N also shows an aromatics complex benzene extraction unit 818 in a crude oil refinery facility. The steam heat input for the raffinate splitter can be 0 MW because the alternative flow path disclosed in this configuration may satisfy the entire heat load for the operation of the raffinate splitter. In an alternative embodiment, the steam heat input for the raffinate splitter can be reduced because the alternative flow path disclosed in this configuration may partially satisfy the heat load for the operation of the raffinate splitter.

In these instances, the first heat exchanger and the seventh heat exchanger (FIG. 1A) are coupled to each other in parallel in regards to the flow of raffinate overheads stream. The second heat exchanger, the fifth heat exchanger and the sixth heat exchanger (FIG. 1G) are coupled to each other in series in regards to the flow of the diesel stripper bottoms stream. The second heat exchanger and the third heat exchanger (FIG. 1J) are coupled to each other in parallel in regards to the flow of sour water stripper bottoms.

In some implementations, the diesel stripper bottoms stream can be flowed in series through the different plants. For example, the diesel stripper bottoms stream is flowed first through the gas separation plant and then the sour water stripper plant. In another implementation, within the gas separation plant the diesel stripper bottoms stream may flow through the de-euthanizer exchanger first and then the C3/C4 splitter exchanger.

FIGS. 1H-1I shows a naphtha hydrotreating plant 814 in a crude oil refinery facility. The naphtha splitter bottoms stream can be flowed in the plant as a single stream and split into multiple streams or it can be flowed into the plant as multiple streams to facilitate heat recovery. As shown in FIG. 1G, a diesel stripper overhead stream can directly heat a first naphtha splitter bottoms stream in heat exchanger A with a thermal duty that can range between about 1 MW and 10 MW (for example, 7.46 MW). The transfer of heat directly to another process stream captures heat that would have otherwise been discharged to the environment. The diesel stripper overhead stream is returned to the diesel hydro-treating plant 800 for further processing.

As shown in FIG. 1A, the raffinate column overheads stream can directly heat a second naphtha splitter bottoms stream in heat exchanger B with a thermal duty that can range between about 5 MW and 15 MW (for example, 8.5 MW). The transfer of heat directly to another process stream captures heat that would have otherwise been discharged to the environment. The first, the second and the third raffinate column overheads streams are recombined and returned to the xylene separation unit 820 for further processing.

As shown in FIG. 1E (represented collectively by FIGS. 1E-1 and 1E-2) (specifically in FIG. 1E-1), a product stripper overhead stream can directly heat a third naphtha splitter bottoms stream in heat exchanger C with a thermal duty that can range between about 1 MW and 10 MW (for example, 3.38 MW). The transfer of heat directly to another process stream captures heat that would have otherwise been discharged to the environment. The product stripper stream is returned to the hydrocracking plant 812 for further processing.

As shown in FIG. 1B, a diesel product stream can directly heat a fourth naphtha splitter stream in heat exchanger D with a thermal duty that can range between about 1 MW and 10 MW (for example, 6.6 MW). The transfer of heat directly to another process stream captures heat that would have otherwise been discharged to the environment. The diesel product stream is returned to the hydrocracking plant 812 for further processing.

As shown in FIG. 1F, a kerosene product stream can directly heat a fifth naphtha splitter bottoms stream in heat exchanger E with a thermal duty that can range between about 1 MW and 10 MW (for example, 5.4 MW). The transfer of heat directly to another process stream captures heat that would have otherwise been discharged to the environment. The kerosene product stream is returned to the hydrocracking plant 812 for further processing.

As shown in FIG. 1E (specifically in FIG. 1E-2), a kerosene pumparound stream can directly heat a sixth naphtha splitter bottoms stream in heat exchanger F with a thermal duty that can range between about 1 MW and 10 MW (for example, 5.7 MW). The transfer of heat directly to another process stream captures heat that would have otherwise been discharged to the environment. The kerosene pumparound stream is returned to the hydrocracking plant 812 for further processing.

As shown in FIGS. 1H and 1I, the steam heat input for the naphtha splitter can be 0 MW because the alternative flow path disclosed in this configuration may satisfy the entire heat load for the operation of the naphtha splitter. In an alternative embodiment, the steam heat input for the naphtha splitter can be reduced because the alternative flow path disclosed in this configuration may partially satisfy the heat load for the operation of the n naphtha splitter.

The heat exchanger A, the heat exchanger B, the heat exchanger C, the heat exchanger D, the heat exchanger E and the heat exchanger F (FIG. 1I) are coupled to each other in parallel in relation to the flow of naphtha splitter bottoms flow. The first heat exchanger, the seventh heat exchanger, and the heat exchanger B (FIG. 1A) are coupled to each other in parallel in regards to the flow of the raffinate column overheads stream.

As shown in FIGS. 1H-1I, the heated naphtha splitter bottoms streams are flowed to the naphtha hydro-treating plant 814. As shown in FIG. 1J, the heated sour water stripper streams are flowed to the sour water stripper plant 810. As shown in FIG. 1M, the heated C3/C4 splitter bottom stream and the de-ethanizer bottom stream are flowed to the gas separation plant 804. As shown in FIG. 1K, the heated amine regeneration unit stripper bottom stream is flowed to the sulfur recovery plant 802. As shown in FIG. 1L, the heated acid gas regenerator bottoms stream is flowed to the amine regeneration plant 806. As shown in FIGS. 1N and 1O, the benzene column bottoms and the raffinate splitter bottoms are flowed to the benzene extraction unit 818.

As shown in FIGS. 1A-1O, the naphtha splitter bottoms stream from the naphtha hydrotreating plant is directly heated by multiple second streams from the aromatics complex xylene products separation unit, the hydrocracking plant, and the diesel hydrotreating plant. In some implementations, one of the sour water stripper bottoms from the sour water stripper plant is directly heated by multiple second streams from the xylene products separation unit and the diesel hydrotreating plant.

Such recovery and reuse of waste heat from the aromatics complex xylene products separation unit, the hydrocracking plant and the diesel hydrotreating plant, can result in decreasing or eliminating the heat energy to heat the streams in the amine regeneration plant, the benzene extraction unit, the naphtha hydro-treating plant, the sour water stripping stripper plant, the sulfur recovery plant, the gas separation plant or combinations of them such as by about 166 MW.

Scheme B

In some implementations, the multiple first streams in multiple first plant in the crude oil refining facility such as those present in the aromatics complex sub-units such as the benzene extraction unit, the sour water stripper plant, the sulfur recovery plant, the amine regeneration plant and the gas separation plant can be heated indirectly using the multiple second streams in a second plant in the other aromatics complex sub-unit including the xylene separation unit, the hydrocracking plant, and the diesel hydrotreating plant. In the same configuration, other multiple first streams in a first plant, such as the naphtha hydrotreating plant, in the crude oil refining facility can be directly heated, for example, using techniques similar to those described earlier, using the diesel hydrotreating plant, the hydrocracking plant, and the aromatics complex xylene products separation unit. In such embodiment, one first plant, such as the naphtha hydrotreating plant, can be directly heated by three second plants, and the other first plants can be heated indirectly by two of the second plants, such as the hydrocracking plant and the aromatics complex xylene products separation unit.

Figure 1P:
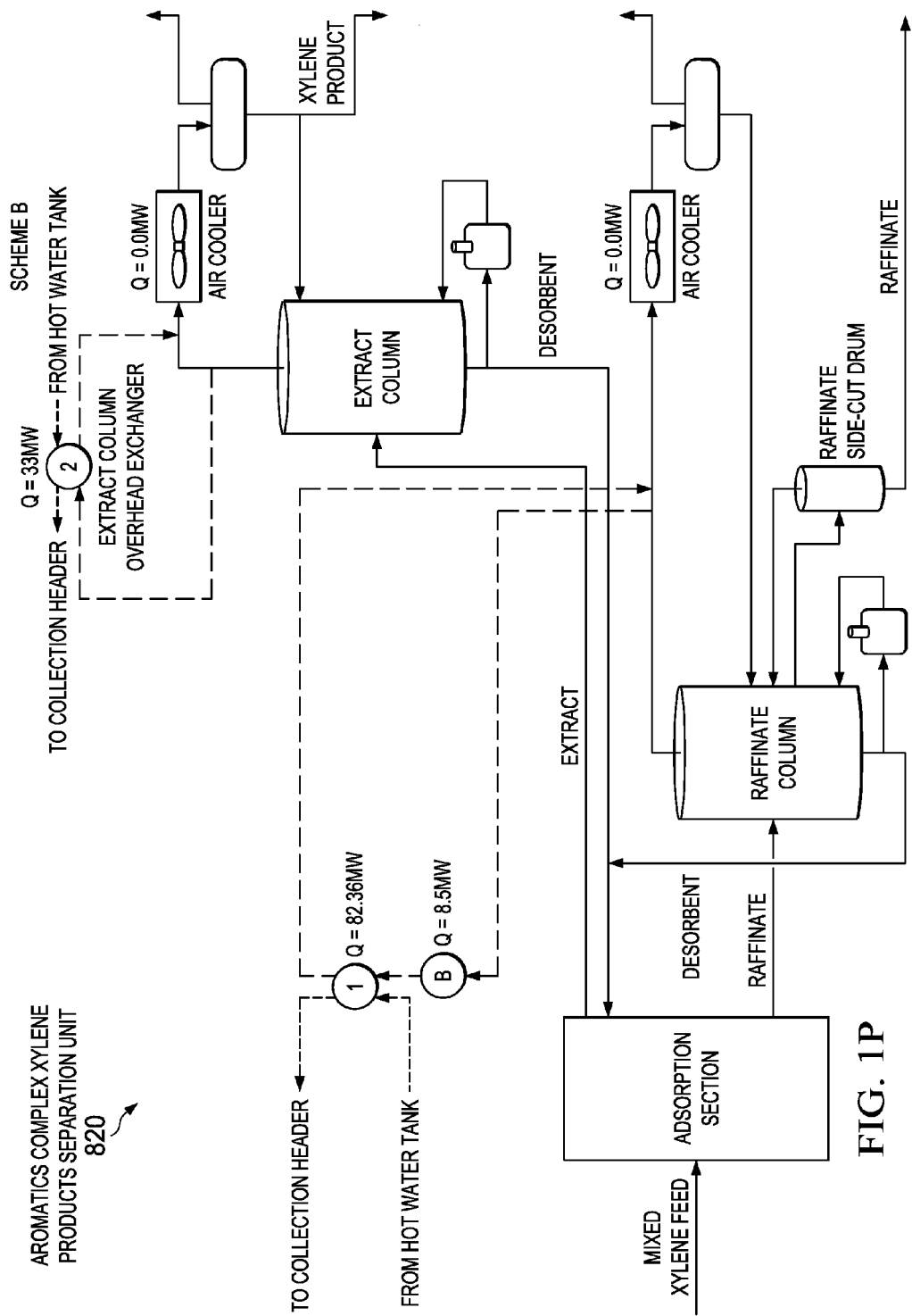

FIGS. 1P-1AC illustrate configurations and related scheme details for thermally integrating different refining plants in the crude oil refining facility. The thermal integration described in these configurations and illustrated in FIGS. 1A-1P can reduce the crude oil refining facility's energy consumption (for example, heating and cooling utilities). For example, a reduction in energy consumption by about 166 MW, for example, 166 MW, can translate to at least about 25%, for example, 25.5%, of the energy consumption in the crude oil refining facility. As described later, the configuration describes a hybrid scheme in which some waste energy is recovered indirectly (that is, using a buffer fluid) and some waste energy is recovered directly (that is, from a process stream).

Indirectly heating the streams can include heating the streams through a buffer fluid, for example, oil, water, or other buffer fluid. A buffer fluid (for example, high pressure water) from a buffer fluid tank (for example, hot water tank) is flowed to the xylene separation unit 820. The buffer fluid can be flowed into the plant as a single stream and split into multiple streams or it can be flowed into the plant as multiple streams.

FIG. 1P shows an aromatics complex xylene products separation unit 820 in a crude oil refining facility. A first buffer fluid can be heated using the raffinate column overheads stream in a first heat exchanger with a thermal duty that can range between about 75 MW and 85 MW (for example, 82.36 MW). The transfer of heat from the process stream into the buffer fluid captures heat that would have otherwise been discharged to the environment. The raffinate column overheads stream is returned to the xylene separation unit 820 for further processing.

A second buffer fluid stream can be heated using the extract column overhead stream in a second heat exchanger with a thermal duty that can range between about 30 MW and 40 MW (for example, 33 MW). The transfer of heat from this process stream into the buffer fluid captures heat that would have otherwise been discharged to the environment. As shown in FIG. 1P, the cooling requirement of the extract column overheads stream can be 0 MW because the alternative flow path disclosed in this configuration may satisfy the entire cooling requirement for the extract column overhead stream for the operation of the extract column. The extract column overheads stream is returned to the xylene separation unit 820 for further processing.

Figure 1Q:
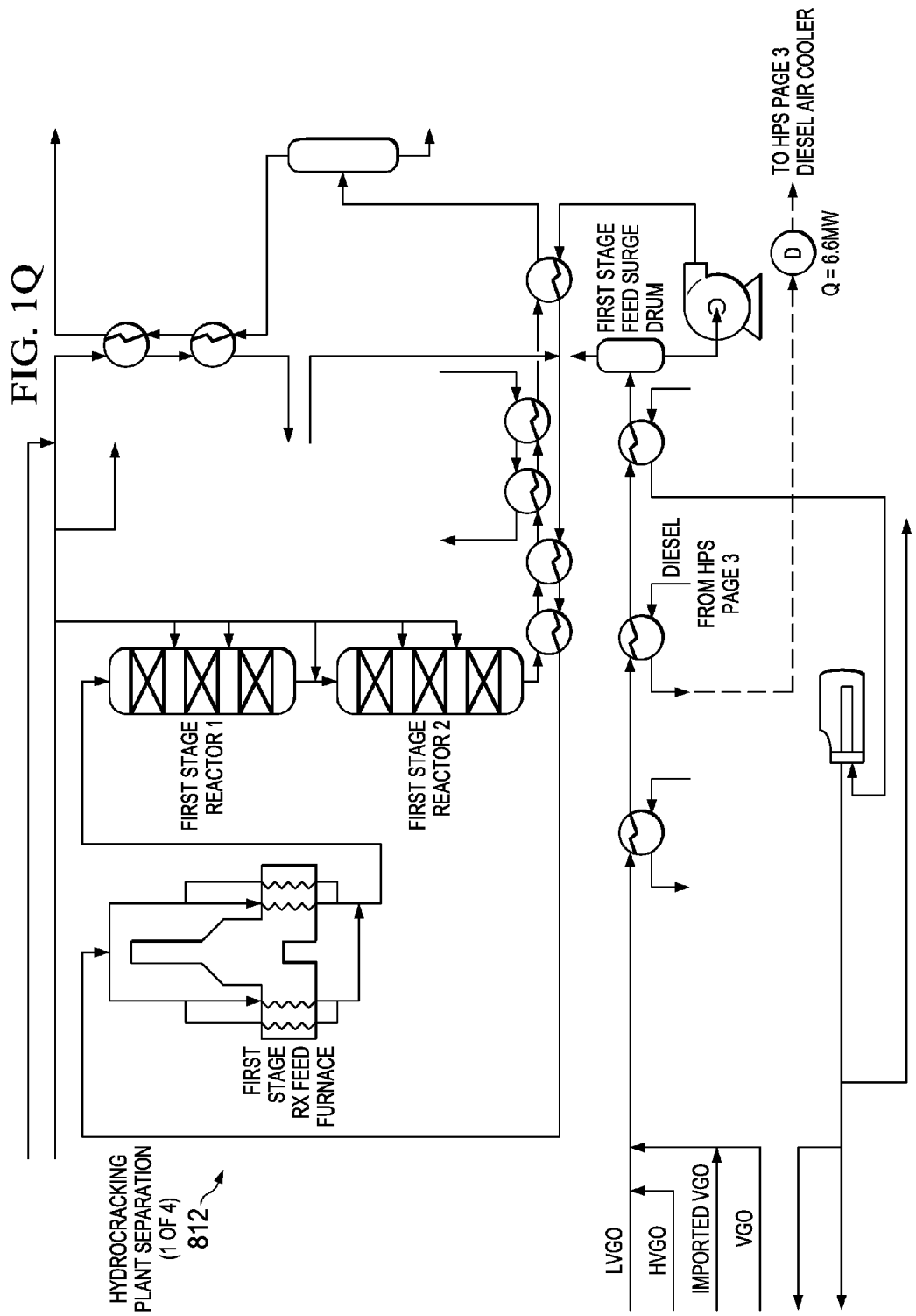
Figure 1R:
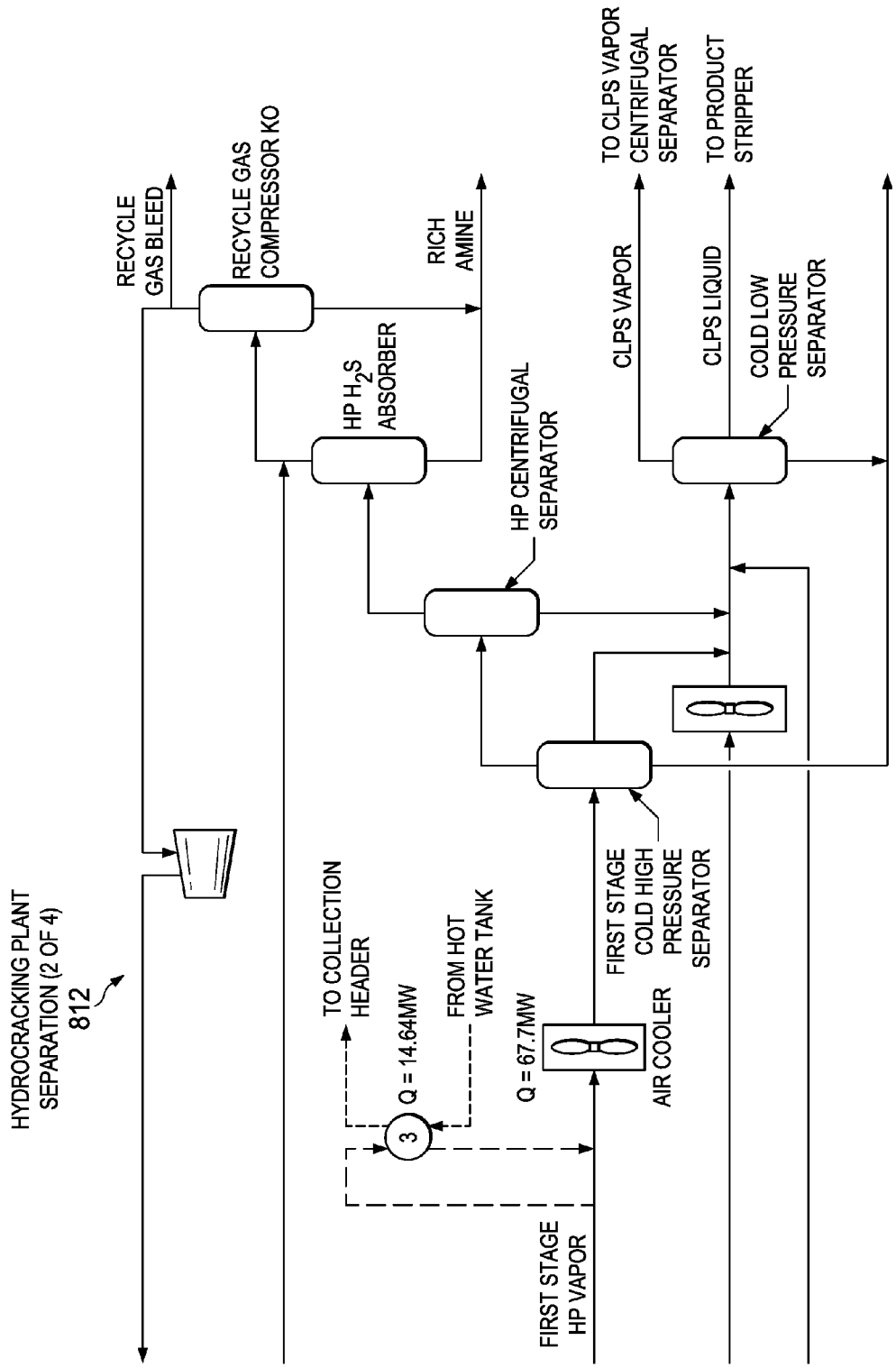

FIGS. 1Q-1T show hydrocracking plant unit 812 in a crude oil refining facility. Specifically, FIG. 1R shows a third buffer fluid stream can be heated using the first stage reaction feed stream to cold high pressure separator in a third heat exchanger with a thermal duty that can range between about 10 MW and 20 MW (for example, 14.64 MW). The transfer of heat from this process stream into the buffer fluid captures heat that would have otherwise been discharged to the environment. The first stage reaction feed stream is flowed to the hydrocracking plant 812 for further processing. In all instances, the buffer fluid absorbs heat that would have otherwise been discharged to the environment.

The first, second, and third heated buffer fluid branches are combined into a combined heated buffer fluid in a collection header. In this manner, the first heat exchanger, the second heat exchanger and the third heat exchanger are coupled to each other in parallel relative to the flow of the buffer fluid.

The combined heated buffer fluid from the collection header (or in some embodiments, a heated or insulated buffer fluid tank or storage unit that can hold heated collected buffer fluid for a period before use) can be flowed to the benzene extraction unit 818, the sour water stripper plant 810, the sulfur recovery plant 802, the amine regeneration plant 806 and the gas separation plant 804.

Figures 1, 1S:
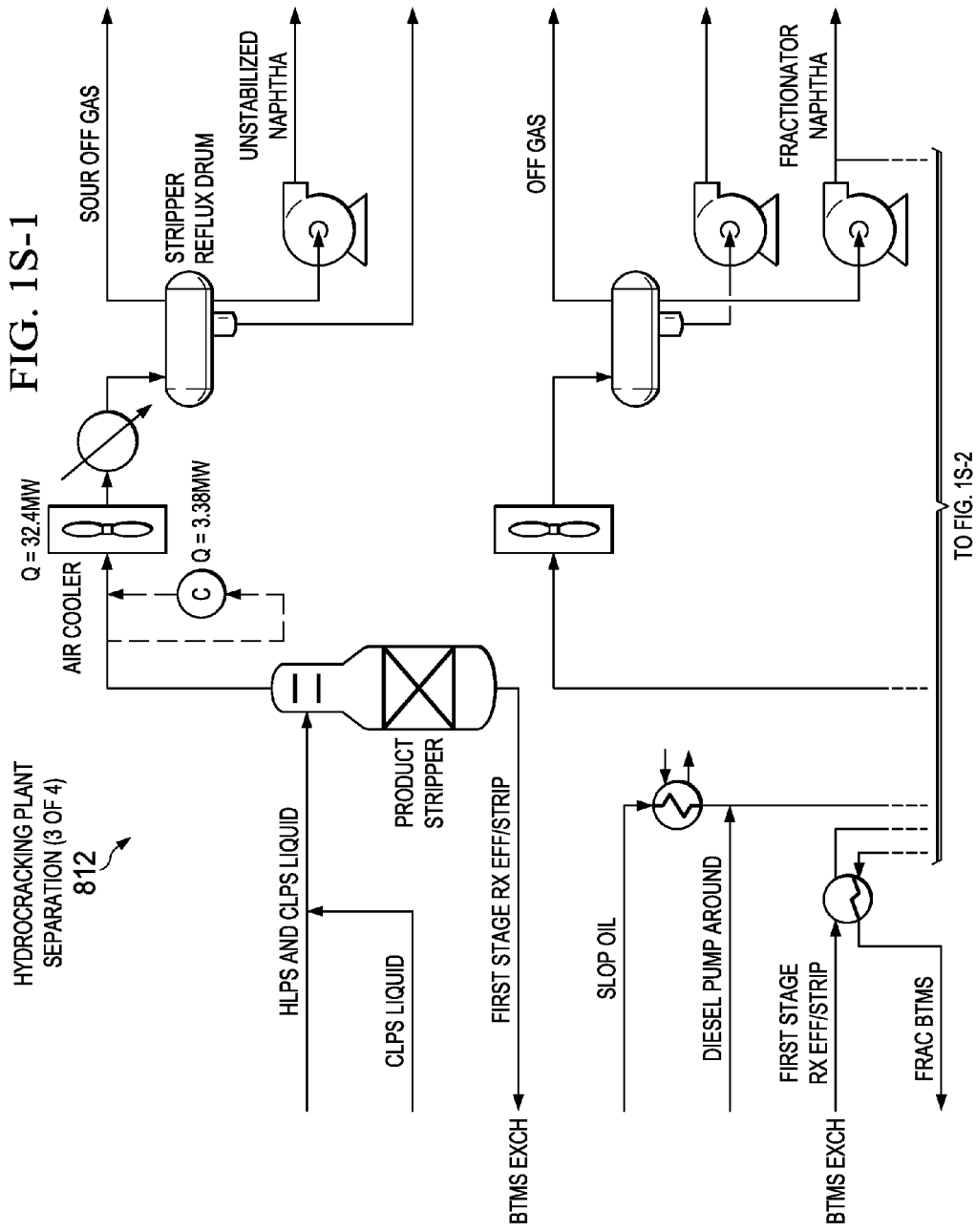
Figures 1, 1S, 2:
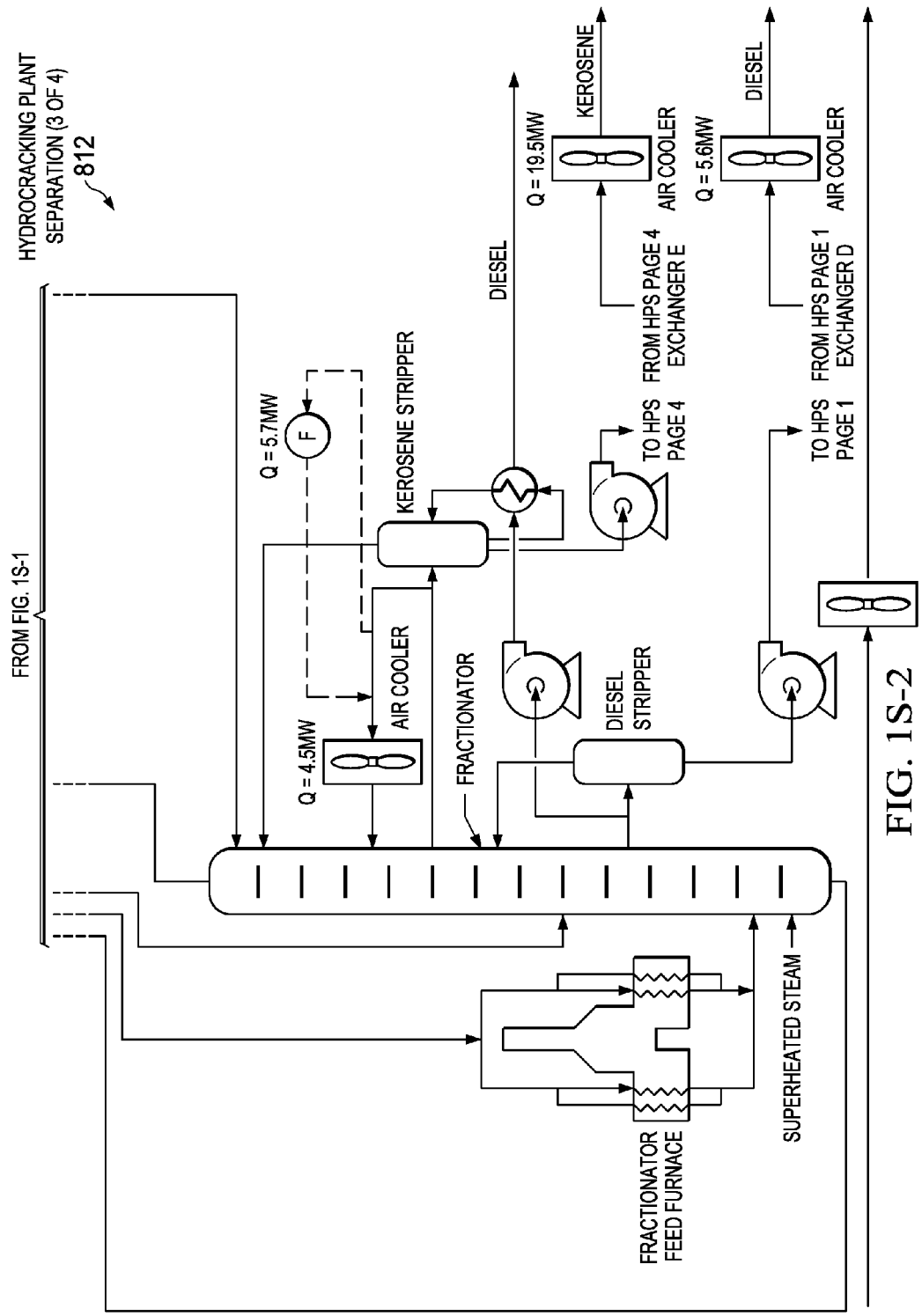
Figure 1T:
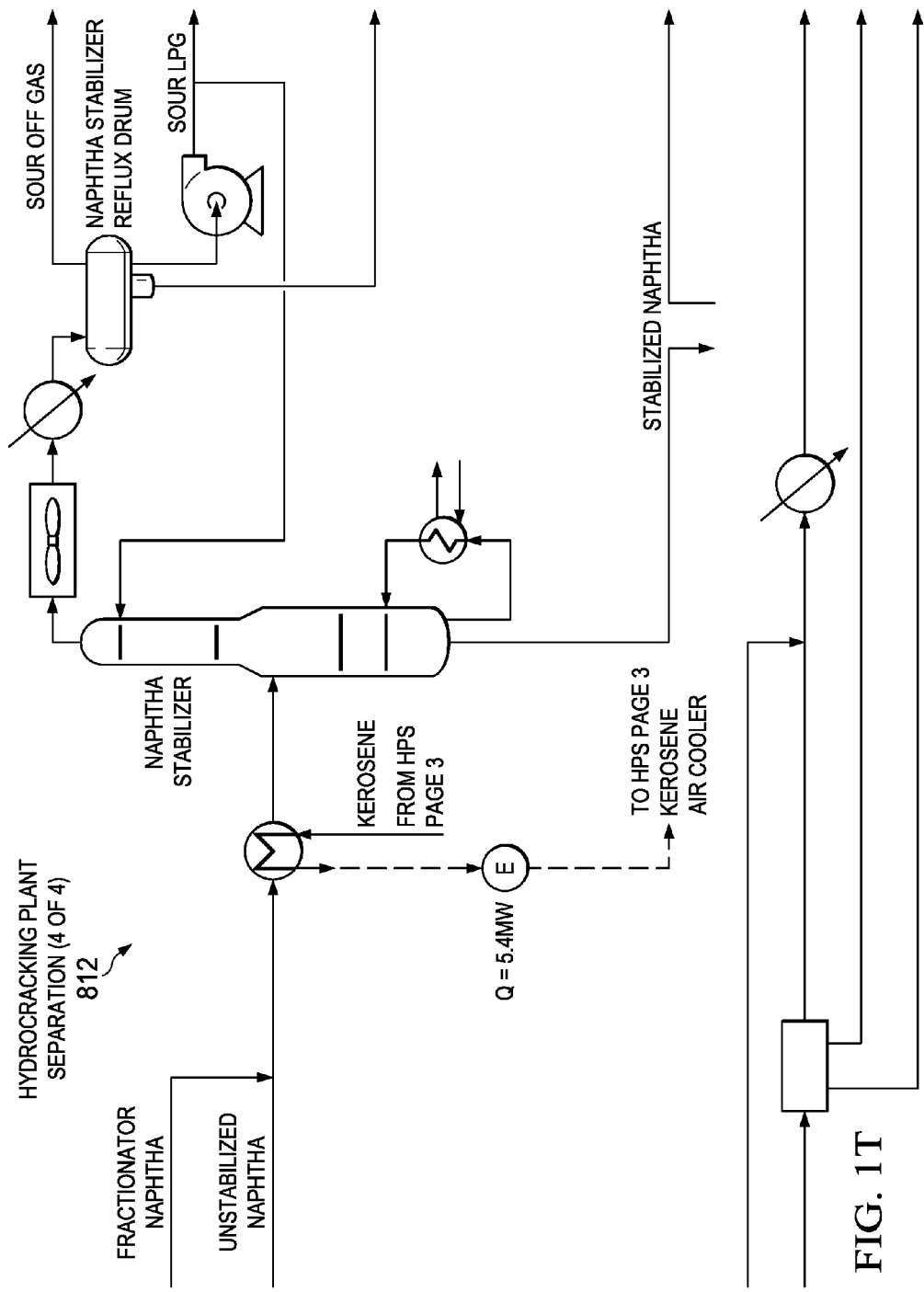
Figure 1U:
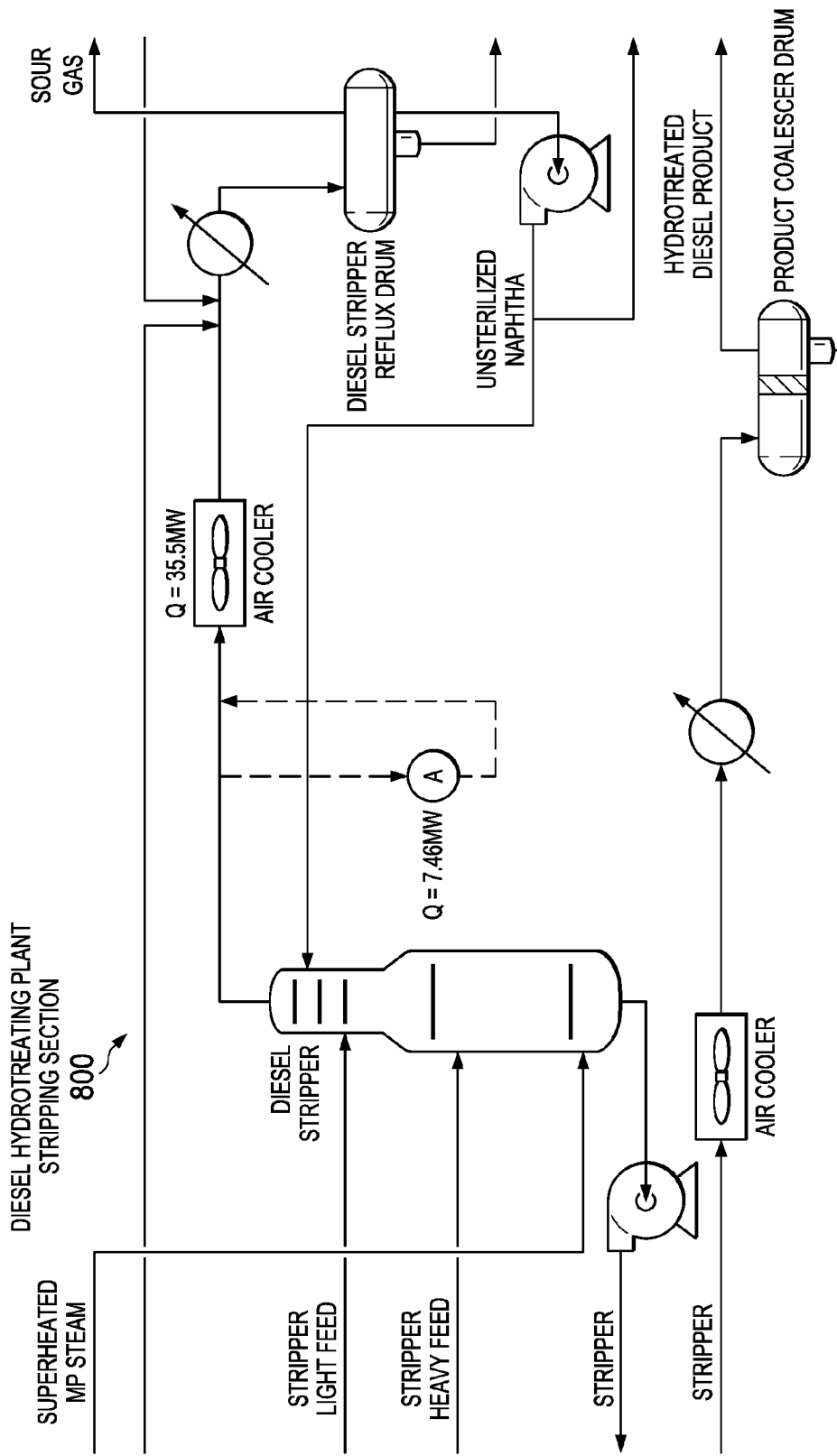

In an embodiment, the buffer fluid is flowed to the aromatics complex benzene extraction unit 818. FIG. 1X shows an aromatics complex benzene extraction unit 818 in a crude oil refining facility. The benzene column bottom stream can be heated using the combined heated buffer fluid in a fourth heat exchanger with a thermal duty that can range between about 1 MW and 10 MW (for example, 6 MW). The fourth heat exchanger is coupled to, in series with and is downstream of the set of the first, second and third heat exchangers relative to the buffer fluid flow.

As shown in FIG. 1X, the steam heat input for the benzene column can be 0 MW because the alternative flow path disclosed in this configuration may satisfy the entire heat load for the operation of the benzene column. In an alternative embodiment, the steam heat input for the benzene column can be reduced because the alternative flow path disclosed in this configuration may partially satisfy the heat load for the operation of the benzene column FIG. 1Y also shows an aromatics complex benzene extraction unit 818 in a crude oil refining facility. A raffinate splitter bottoms stream can be heated in a fifth heat exchanger with a thermal duty that can range between about 5 MW and 15 MW (for example, 8.6 MW) using the heated buffer fluid exiting the fourth heat exchanger (FIG. 1Y). The fifth heat exchanger is coupled to, in series with and is downstream of the set of the first, second and third heat exchangers relative to the buffer fluid flow.

As shown in FIG. 1Y, the steam heat input for the raffinate splitter can be 0 MW because the alternative flow path disclosed in this configuration may satisfy the entire heat load for the operation of the raffinate splitter. In an alternative embodiment, the steam heat input for the raffinate splitter can be reduced because the alternative flow path disclosed in this configuration may partially satisfy the heat load for the operation of the raffinate splitter.

Figure 1V:
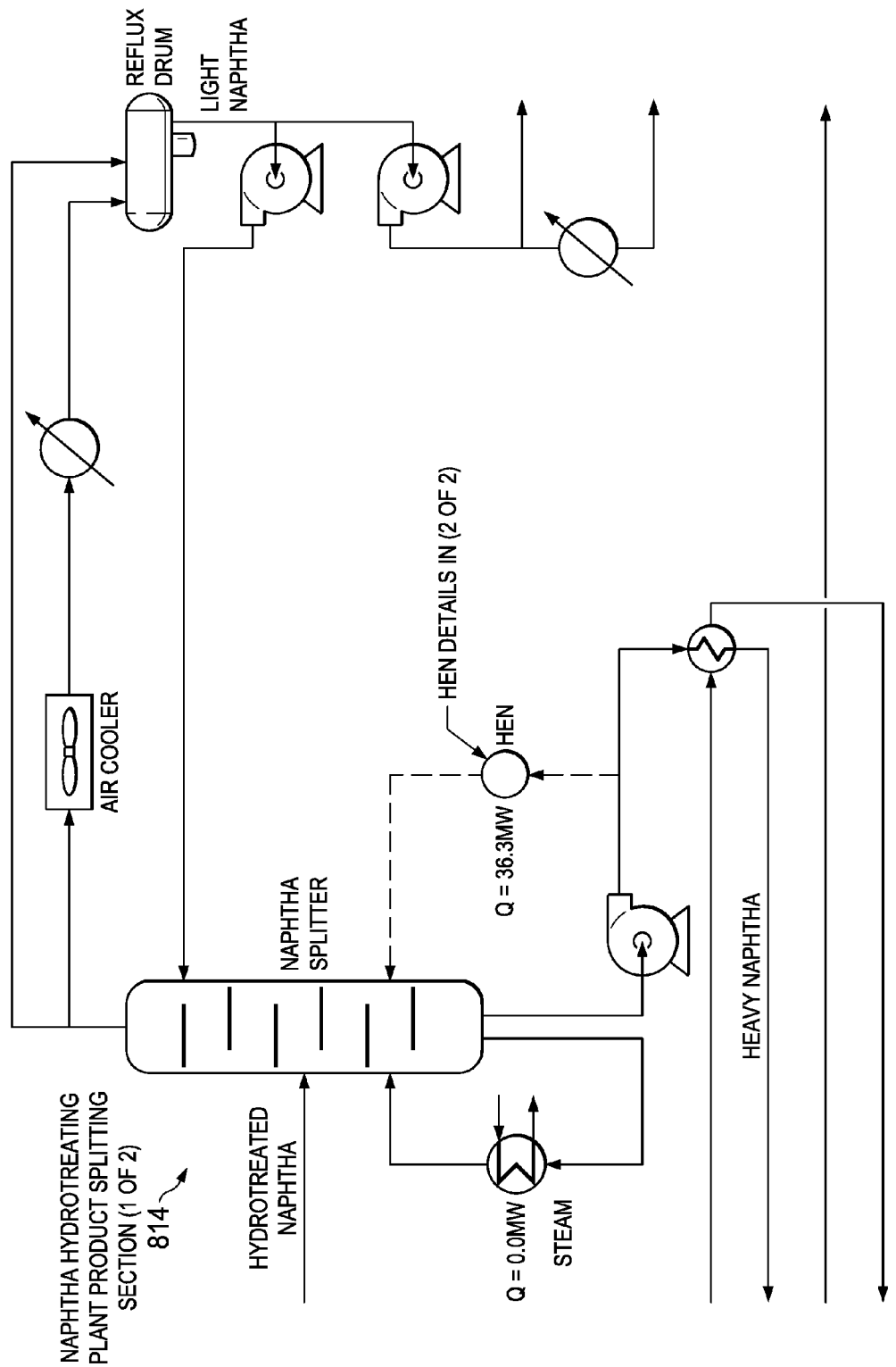
Figure 1W:
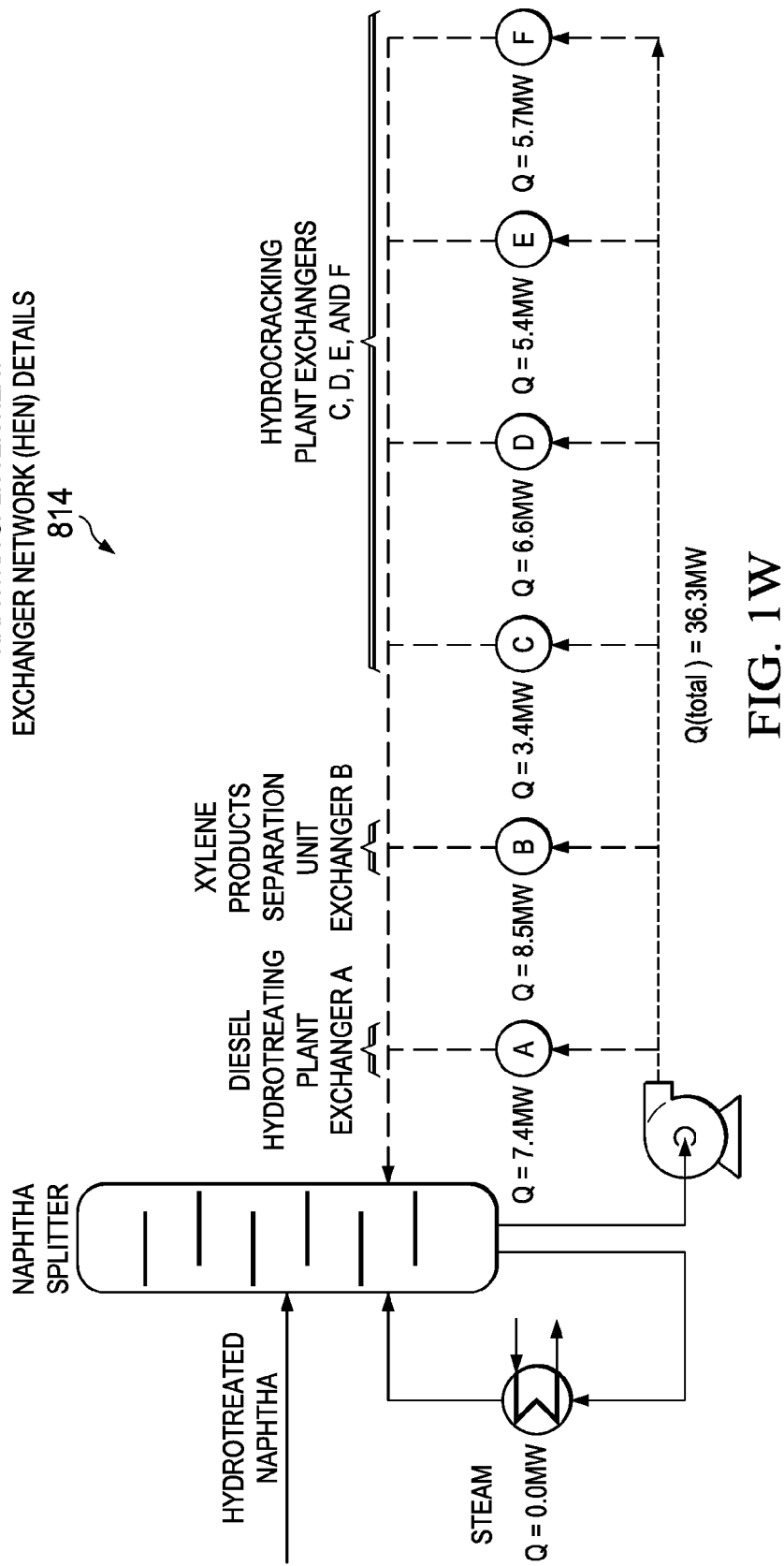
Figure 1X:
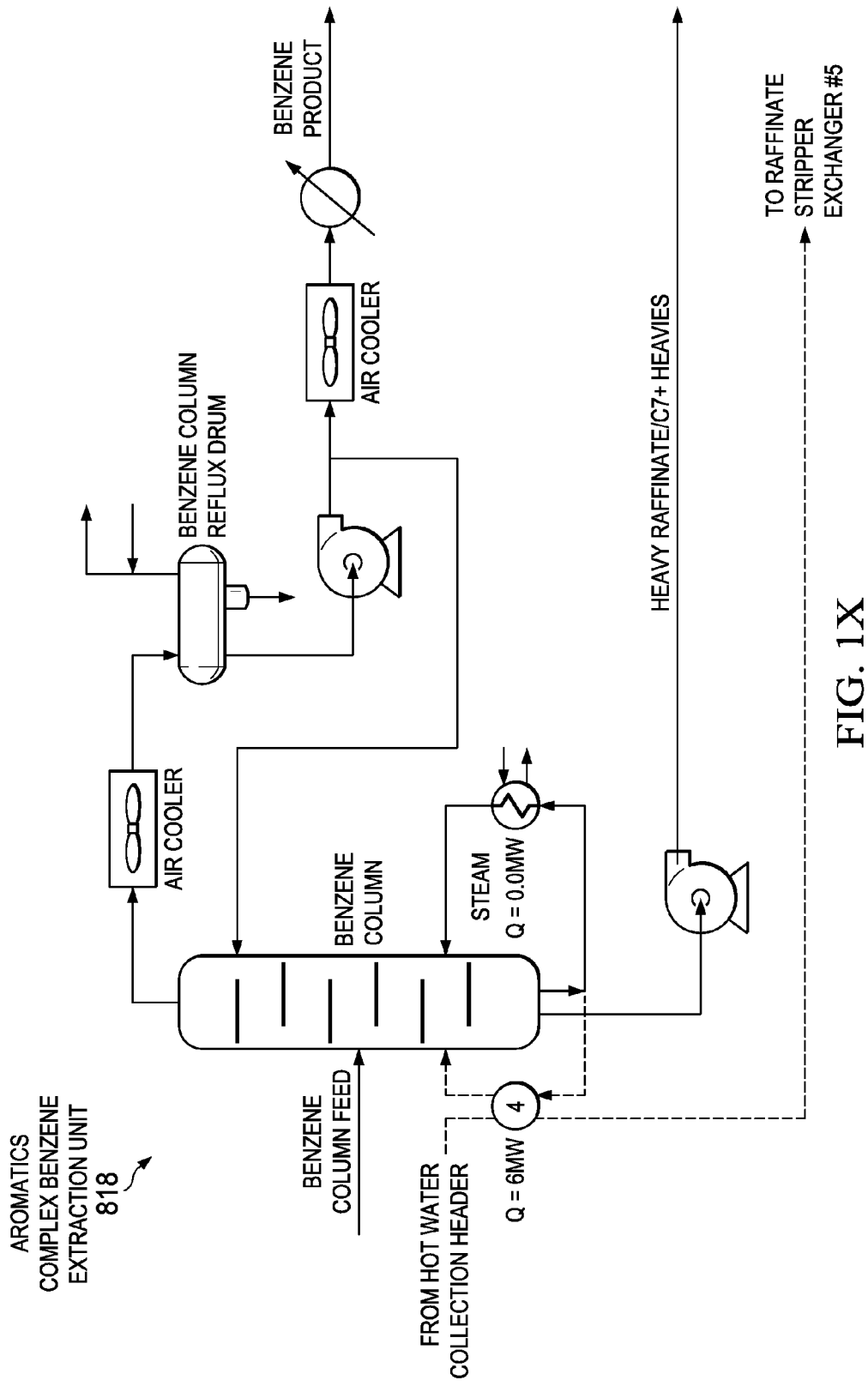
Figure 1Y:
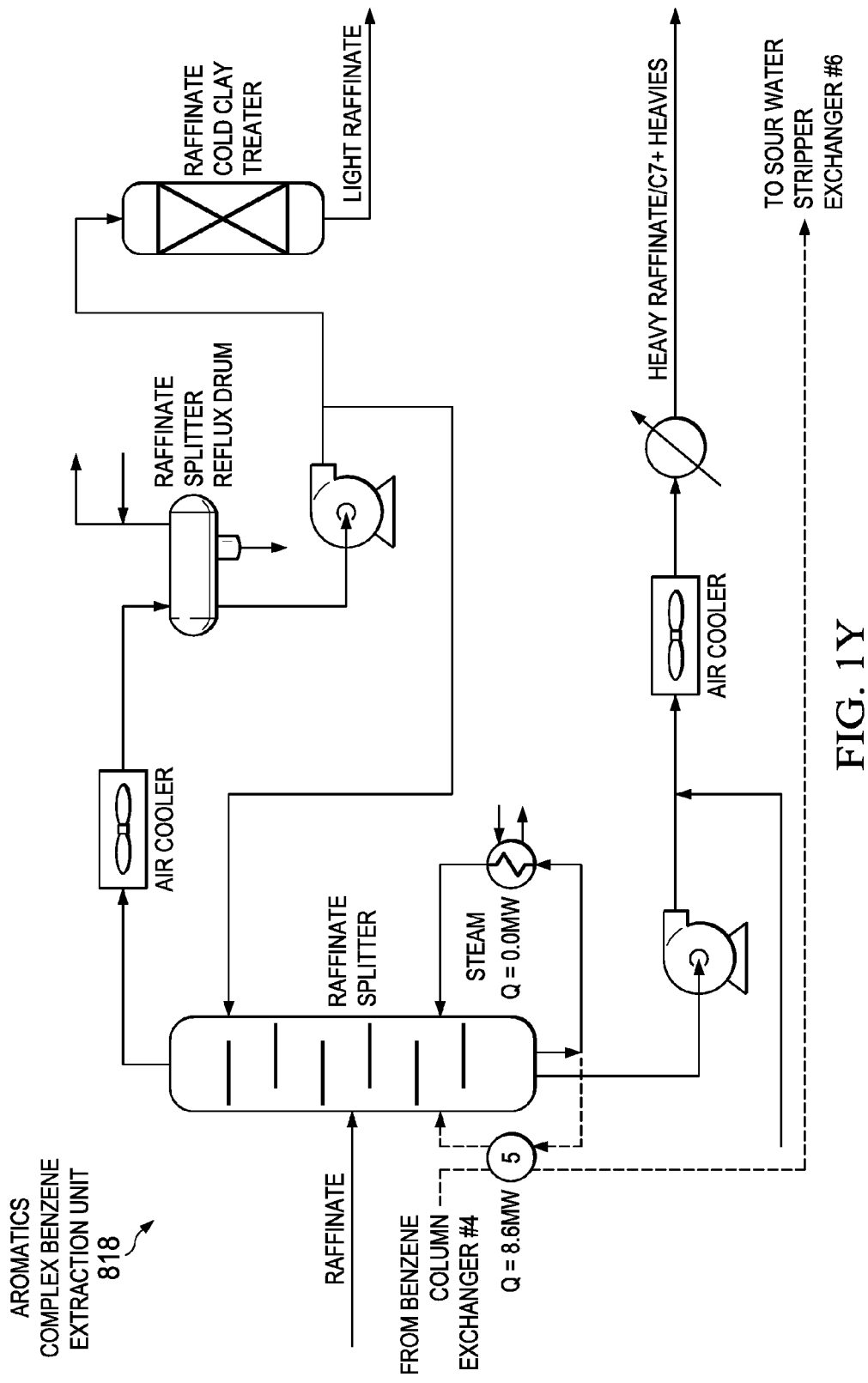
Figure 1Z:
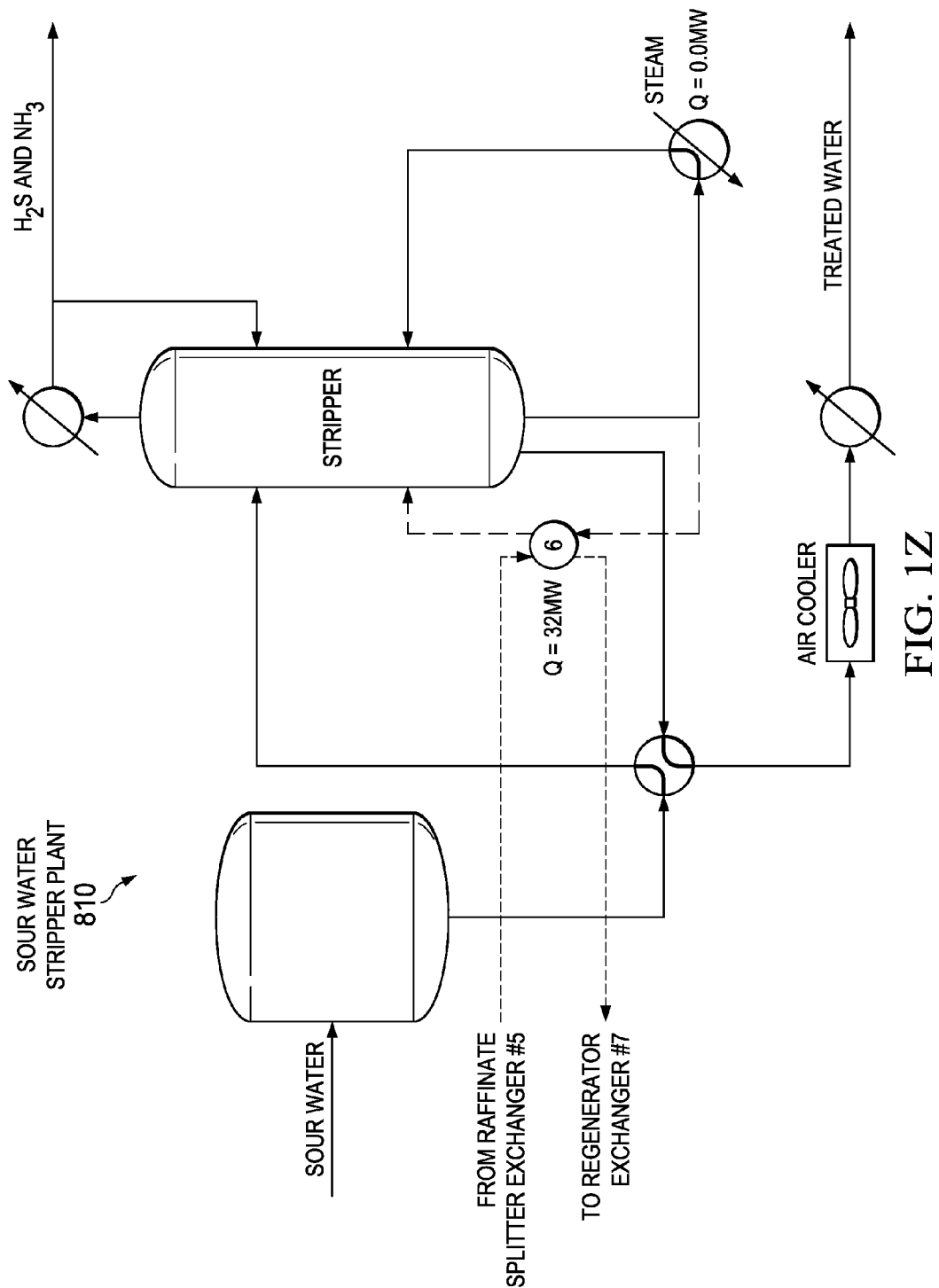
Figure 1A:
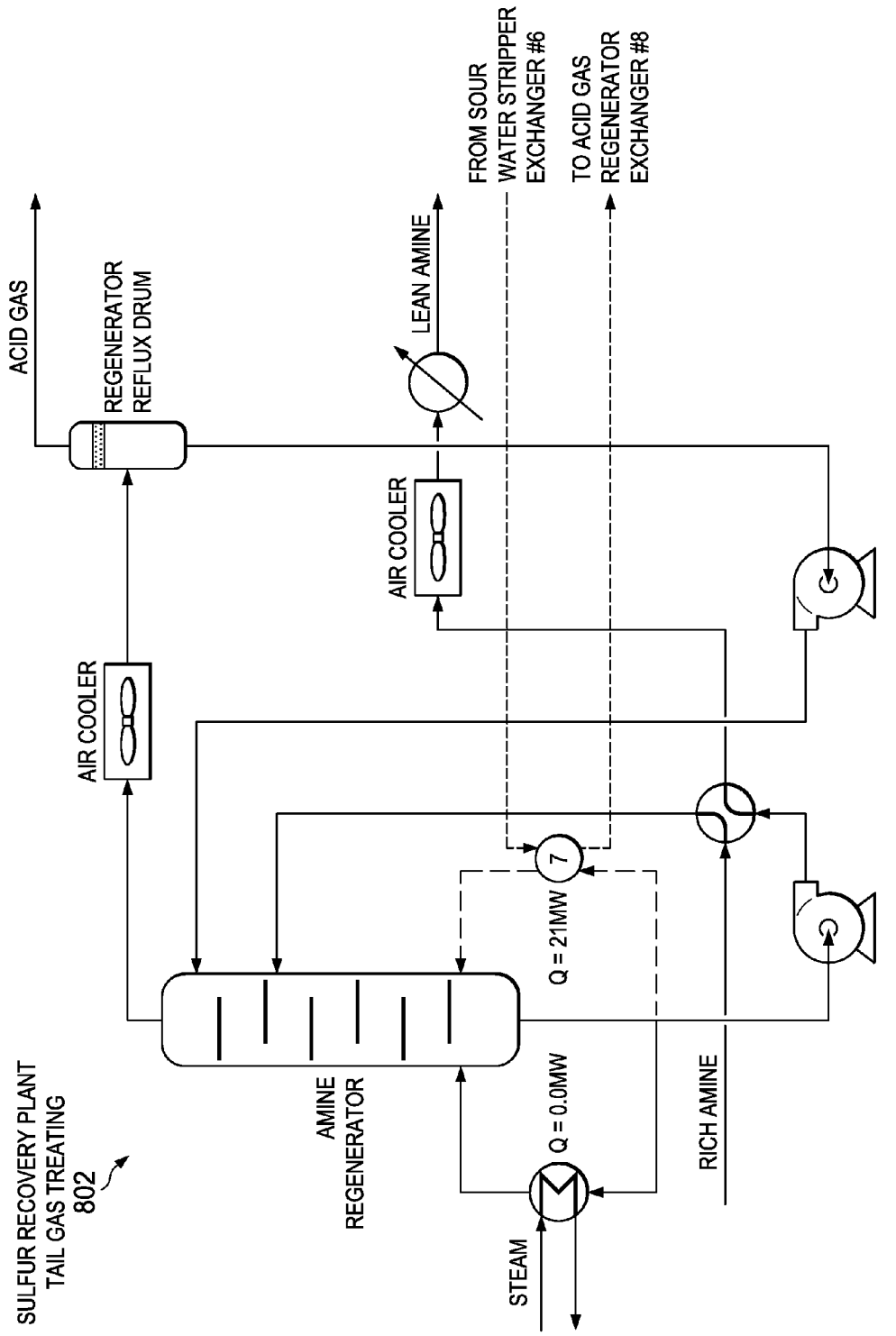
Figure 1A:
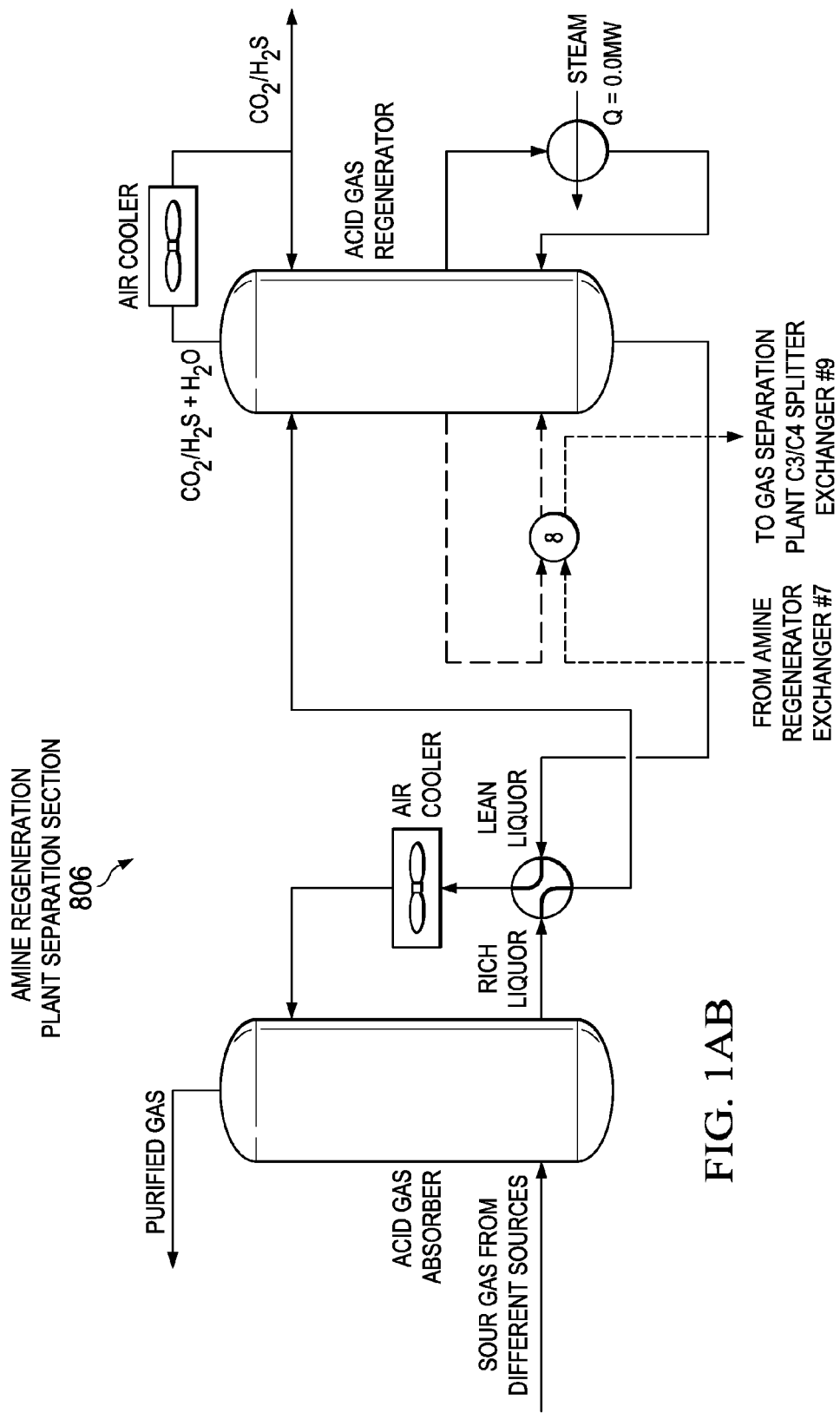
Figure 1A:
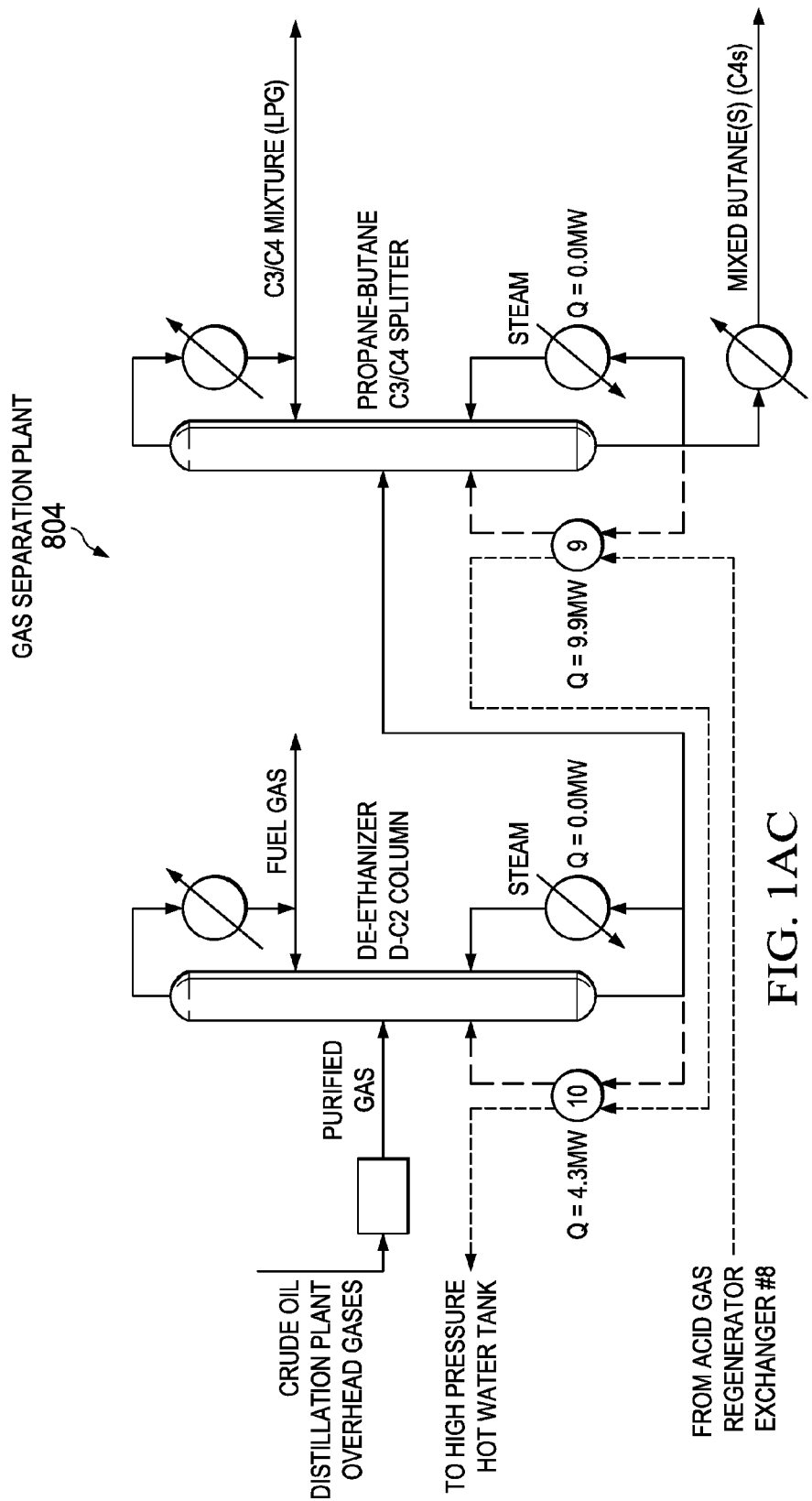

FIG. 1Z also shows a sour water stripper plant 810 in a crude oil refining facility. A sour water stripper bottom stream can be heated using the heated buffer fluid in a sixth heat exchanger with a thermal duty that can range between about 25 MW and 35 MW (for example, 32 MW). The sixth heat exchanger is coupled to, in series with and is downstream of the set of the first, second and third heat exchangers relative to the buffer fluid flow.

As shown in FIG. 1Z, the steam heat input for the sour water stripper can be 0 MW because the alternative flow path disclosed in this configuration may satisfy the entire heat load for the operation of the sour water stripper. In an alternative embodiment, the steam heat input for the sour water stripper can be reduced because the alternative flow path disclosed in this configuration may partially satisfy the heat load for the operation of the sour water stripper.

FIG. 1AA also shows a sulfur recovery plant 802 in a crude oil refining facility. An amine regenerator bottoms stream can be heated using the heated buffer fluid in a seventh heat exchanger with a thermal duty that can range between about 15 MW and 25 MW (for example, 21 MW). The seventh heat exchanger is coupled to, in series with and is downstream of the set of the first, second and third heat exchangers relative to the buffer fluid flow.

As shown in FIG. 1AA, the steam heat input for the amine regenerator can be 0 MW because the alternative flow path disclosed in this configuration may satisfy the entire heat load for the operation of the amine regenerator. In an alternative embodiment, the steam heat input for the amine regenerator can be reduced because the alternative flow path disclosed in this configuration may partially satisfy the heat load for the operation of the amine regenerator.

FIG. 1AB also shows an amine regeneration plant 806 in a crude oil refining facility. An acid gas regenerator bottoms stream can be heated using the heated buffer fluid in an eighth heat exchanger with a thermal duty that can range between about 45 MW and 55 MW (for example, 47.8 MW). The eighth heat exchanger is coupled to, in series with and is downstream of the set of the first, second and third heat exchangers relative to the buffer fluid flow.

As shown in FIG. 1AB, the steam heat input for the acid gas regenerator can be 0 MW because the alternative flow path disclosed in this configuration may satisfy the entire heat load for the operation of the acid gas regenerator. In an alternative embodiment, the steam heat input for the acid gas regenerator can be reduced because the alternative flow path disclosed in this configuration may partially satisfy the heat load for the operation of the acid gas regenerator.

FIG. 1AC also shows a gas separation plant 804 in a crude oil refining facility. A C3/C4 splitter bottoms stream can be heated using the heated buffer fluid in a ninth heat exchanger with a thermal duty that can range between about 5 MW and 15 MW (for example, 9.9 MW). The ninth heat exchanger is coupled to, in series with and is downstream of the set of the first, second and third heat exchangers relative to the buffer fluid flow.

As shown in FIG. 1AC, the steam heat input for the C3/C4 splitter can be 0 MW because the alternative flow path disclosed in this configuration may satisfy the entire heat load for the operation of the C3/C4 splitter. In an alternative embodiment, the steam heat input for the C3/C4 splitter can be reduced because the alternative flow path disclosed in this configuration may partially satisfy the heat load for the operation of the C3/C4 splitter.

Also as shown in FIG. 1AC, t de-ethanizer bottoms stream can be heated using the heated buffer fluid with a thermal duty that can range between about 1 MW and 10 MW (for example, 4.3 MW). The tenth heat exchanger is coupled to, in series with and is downstream of the set of the first, second and third heat exchangers relative to the buffer fluid flow. The tenth heat exchanger is coupled to, in series with and is downstream of the set of the first, second and third heat exchangers relative to the buffer fluid flow.

As shown in FIG. 1AC, the steam heat input for the de-ethanizer column can be 0 MW because the alternative flow path disclosed in this configuration may satisfy the entire heat load for the operation of the de-ethanizer column. In an alternative embodiment, the steam heat input for the de-ethanizer column can be reduced because the alternative flow path disclosed in this configuration may partially satisfy the heat load for the operation of the de-ethanizer column.

The heated buffer fluid exiting the tenth heat exchanger is flowed to the collection header or the buffer fluid tank. In this manner, the fourth heat exchanger, the fifth heat exchanger, the sixth heat exchanger, the seventh heat exchanger, the eighth heat exchanger, the ninth heat exchanger and the tenth heat exchanger are fluidically coupled to each other in series.

In some implementations, the heated buffer fluid can be flowed in series through the different plants. For example, the heated buffer fluid can be flowed first to the benzene extraction unit, then to the sour water stripper plant, then to the sulfur recovery plant, then to the amine regeneration plant, and then to the gas separation plant. In another implementation, within the gas separation plant the heated buffer fluid stream may flow through the de-ethanizer exchanger first and then the C3/C4 splitter exchanger. The heated buffer fluid exiting the tenth heat exchanger can be flowed to a buffer fluid tank. The buffer fluid from the buffer fluid tank can then be flowed to the different plants to restart the waste heat recovery and reuse cycle.

FIGS. 1V-1W shows a naphtha hydrotreating plant 814 in a crude oil refinery facility. The naphtha splitter bottoms stream can be flowed in the plant as a single stream and split into multiple streams or it can be flowed into the plant as multiple streams to facilitate heat recovery. As shown in FIG. 1U, a diesel stripper overheads stream can directly heat a first stream of the naphtha splitter bottoms in heat exchanger A with a thermal duty that can range between about 1 MW and 10 MW (for example, 7.46 MW). The transfer of heat directly to another process stream captures heat that would have otherwise been discharged to the environment. The diesel stripper overheads stream is returned to the diesel hydro-treating plant 800 for further processing.

As shown in FIG. 1P, the raffinate column overheads stream can directly heat a second naphtha splitter column bottoms stream in heat exchanger B with a thermal duty that can range between about 5 MW and 15 MW (for example, 8.5 MW). The transfer of heat directly to another process stream captures heat that would have otherwise been discharged to the environment. The first heat exchanger and the heat exchanger B are coupled to each other in series in regards to the flow of the raffinate column overheads stream, and in this instance the first heat exchanger is downstream of heat exchanger B. As shown in FIG. 1P, the cooling requirement of the raffinate column overheads stream can be 0 MW because the alternative flow path disclosed in this configuration may satisfy the entire cooling requirement for the raffinate column overhead stream for the operation of the raffinate column. The raffinate column overhead stream is returned to the xylene separation unit 820 for further processing.

In some implementations, the raffinate column overheads stream can be flowed in series through the different plants. For example, the raffinate column overheads stream is flowed first through the buffer fluid heat exchanger and then through the naphtha hydrotreating plant.

As shown in FIG. 1S (represented collectively by FIGS. 1S-1 and 1S-2) (specifically FIG. 1S-1), a product stripper overheads stream can directly heat a third naphtha splitter bottoms stream in heat exchanger C with a thermal duty that can range between about 1 MW and 10 MW (for example, 3.38 MW). The transfer of heat directly to another process stream captures heat that would have otherwise been discharged to the environment. The product stripper overheads stream is returned to the hydrocracking plant 812 for further processing.

As shown in FIG. 1Q, a diesel product stream can directly heat a fourth naphtha splitter bottoms stream in heat exchanger D with a thermal duty that can range between about 1 MW and 10 MW (for example, 6.6 MW). The transfer of heat directly to another process stream captures heat that would have otherwise been discharged to the environment. The diesel product stream is returned to the hydrocracking plant 812 for further processing.

As shown in FIG. 1T, a kerosene product stream can directly heat a fifth naphtha splitter bottoms stream in heat exchanger E with a thermal duty that can range between about 1 MW and 10 MW (for example, 5.4 MW). The transfer of heat directly to another process stream captures heat that would have otherwise been discharged to the environment. The kerosene product stream is returned to the hydrocracking plant 812 for further processing.

As shown in FIG. 1S (specifically FIG. 1S-2), a kerosene pumparound stream can directly heat a sixth naphtha splitter bottoms stream in heat exchanger F with a thermal duty that can range between about 1 MW and 10 MW (for example, 5.7 MW). The transfer of heat directly to another process stream captures heat that would have otherwise been discharged to the environment. The kerosene pumparound stream is returned to the hydrocracking plant 812 for further processing.

As shown in both FIGS. 1V and 1W, the steam heat input for the naphtha splitter can be 0 MW because the alternative flow path disclosed in this configuration may satisfy the entire heat load for the operation of the naphtha splitter. In an alternative embodiment, the steam heat input for the naphtha splitter can be reduced because the alternative flow path disclosed in this configuration may partially satisfy the heat load for the operation of the naphtha splitter.

As shown in FIGS. 1P-1AC, the naphtha splitter bottoms stream from the naphtha hydrotreating plant is directly heated by multiple second streams from the aromatics complex xylene products separation unit, the hydrocracking plant, and the diesel hydrotreating plant. The heat exchanger A, the heat exchanger B, the heat exchanger C, the heat exchanger D, the heat exchanger E and the heat exchanger F are coupled to each other in parallel with respect to the flow of the naphtha splitter bottoms.

Such recovery and reuse of waste heat indirectly from both the aromatics complex xylene products separation unit and the hydrocracking plant and directly from the aromatics complex, the diesel hydrotreating plant and the hydrocracking plant can result in decreasing or eliminating the heat energy to heat the streams in the amine regeneration plant, the benzene extraction unit, the naphtha hydrotreating plant, the sour water stripper plant, the sulfur recovery plant, the gas separation plant or combinations of them such as by about 166 MW.

In summary, this disclosure describes configurations and related processing schemes of specific direct or indirect inter-plants and hybrid, intra- and inter-plants integration for energy consumption reduction synthesized for grassroots medium grade crude oil semi-conversion refineries to increase energy efficiency from specific portions of low grade waste heat sources. The disclosure also describes configurations and related processing schemes of specific direct or indirect inter-plants integration for energy consumption reduction synthesized for integrated medium grade crude oil semi-conversion refineries and aromatics complex for increasing energy efficiency from specific portions of low grade waste sources.

The economics of industrial production, the limitations of global energy supply, and the realities of environmental conservation are concerns for all industries. It is believed that the world's environment has been negatively affected by global warming caused, in part, by the release of GHG into the atmosphere. Implementations of the subject matter described here can alleviate some of these concerns, and, in some cases, prevent certain refineries, which are having difficulty in reducing their GHG emissions, from having to shut down. By implementing the techniques described here, specific plants in a refinery or a refinery, as a whole, can be made more efficient and less polluting by recovery and reusing from specific portions of low grade waste heat sources.

Thus, particular implementations of the subject matter have been described. Other implementations are within the scope of the following claims.

The invention claimed is:

1. A method implemented in a crude oil refining facility, the method comprising:
heating a first plurality of streams in a first plurality of plants in a crude oil facility using a second plurality of streams in a second plurality of plants in the crude oil refining facility using a plurality of heat exchangers that receive at least one of the first plurality of streams and at least one of the second plurality of streams, wherein the first plurality of plants comprises an amine regeneration plant comprising an acid gas regenerator bottoms stream comprising a weak amine salt, an aromatics complex benzene extraction unit benzene column bottoms stream, a raffinate column bottom stream, a naphtha splitter column bottom stream, the aromatics complex comprising at least one of benzene, toluene or xylene, a sour water stripper plant comprising a stripper bottom stream, a sulfur recovery plant comprising an amine regenerator bottoms stream, a gas separation plant comprising a C3/C4 splitter column bottom stream and a de-ethanizer column bottoms stream, wherein a stream in the gas separation plant comprises at least one of C2 to C4 flows, and wherein the second plurality of plants comprises an aromatics plant xylene products separation unit comprising a raffinate column overheads stream and an extract column overheads stream, a hydrocracking plant comprising a second stage reaction cold high pressure separator, a product stripper stream, a diesel product stream, a kerosene product cooling stream from a main fractionator column, a kerosene pumparound stream, a first stage reaction feed stream to a cold high pressure separator, and a diesel hydro-treating plant.

2. The method of claim 1, wherein heating the first plurality of streams comprises directly heating the first plurality of streams using the second plurality of streams.

3. The method of claim 2, wherein directly heating the stream comprises:
heating, in a first heat exchanger, the acid gas regenerator bottoms stream in the amine regeneration plant using a branch of raffinate column overheads stream in the aromatics plant xylene products separation unit;
heating, in a second heat exchanger, a branch of the stripper bottom stream in the sour water stripper plant using a diesel stripper bottom stream in the diesel hydro-treating plant;
heating, in a third heat exchanger, a branch of the stripper bottom stream using a branch of the extract column overheads stream in the aromatics plant xylene products separation unit;
heating, in a fourth heat exchanger, a branch of the amine regenerator bottoms stream in the sulfur recovery plant using a feed stream to a first stage reaction cold high pressure separator;
heating, in a fifth heat exchanger, a branch of the C3/C4 splitter column bottom stream in the gas separation plant using the diesel stripper bottom stream exiting the second heat exchanger;
heating, in a sixth heat exchanger, a branch of the de-ethanizer column bottoms stream in the gas separation plant using the diesel stripper bottom stream exiting the fifth heat exchanger;
heating, in a seventh heat exchanger, a branch of the benzene column bottoms stream in the aromatics complex benzene extraction unit using a branch of the raffinate column overheads stream; and
heating, in an eighth heat exchanger, a branch of the raffinate column bottom stream in the aromatics complex benzene extraction unit using a feed stream to the second stage reaction cold high pressure separator in the hydrocracking plant.

4. The method of claim 3, wherein the first heat exchanger and the seventh heat exchanger are fluidically coupled to each other in parallel, wherein the second heat exchanger, the fifth heat exchanger and the sixth heat exchanger are fluidically coupled to each other in series, wherein the second heat exchanger and the third heat exchanger are fluidically coupled to each other in parallel.

5. The method of claim 4, wherein the heat exchanger, the heat exchanger B, the heat exchanger C, the heat exchanger D, the heat exchanger E and the heat exchanger F are fluidically coupled to each other in parallel, wherein the heat exchanger B and a combination of the first heat exchanger and the seventh heat exchanger are fluidically coupled to each other in series.

6. The method of claim 3, wherein directly heating the stream comprises:
heating, in heat exchanger A, a branch of the naphtha splitter column bottoms stream using a diesel stripper overhead stream in the diesel hydro-treating plant;
heating, in heat exchanger B, a branch of the naphtha splitter column bottom stream in the aromatics complex benzene extraction unit using the raffinate column overheads stream;
heating, in heat exchanger C, a branch of the naphtha splitter bottoms stream using the product stripper stream in the hydrocracking plant;
heating, in heat exchanger D, a branch of the naphtha splitter bottoms stream using the diesel product stream in the hydrocracking plant;
heating, in heat exchanger E, a branch of the naphtha splitter bottoms stream using the kerosene product cooling stream from the main fractionator column in the hydrocracking plant; and
heating, in heat exchanger F, a branch of the naphtha splitter bottoms stream using the kerosene pumparound stream in the hydrocracking plant.

7. The method of claim 6, wherein the branches of the naphtha splitter bottoms stream are flowed in parallel to the heat exchanger A, the heat exchanger B, the heat exchanger C, the heat exchanger D, the heat exchanger E and the heat exchanger F.

8. The method of claim 6 further comprising:
flowing the branches of the heated naphtha splitter bottoms stream to the aromatics complex benzene extraction unit;
flowing the branches of the branches of the heated stripper bottom stream to the sour water stripper plant;
flowing the branches of the heated C3/C4 splitter bottom streams and the de-ethanizer column bottoms stream to the gas separation plant;
flowing the branches of the heated amine regenerator bottoms stream to the sulfur recovery plant; and
flowing the branches of the heated acid gas regenerator bottoms streams to the amine regeneration plant.

9. The method of claim 1, wherein heating the first plurality of streams comprises indirectly heating the first plurality of streams using the second plurality of streams.

10. The method of claim 9, wherein the buffer fluid comprises at least one of oil or water.

11. The method of claim 9, wherein heating the first plurality of streams comprises indirectly heating the first plurality of streams through a buffer fluid using the second plurality of streams.

12. The method of claim 11, wherein indirectly heating the first plurality of streams through the buffer fluid comprises:
heating, in a first heat exchanger, a branch of the buffer fluid using a raffinate column overheads stream;
heating, in a second heat exchanger, a branch of the buffer fluid using the extract column overheads stream in the aromatics plant xylene products separation unit;
heating, in a third heat exchanger, a branch of the buffer fluid using the first stage reaction feed stream to a cold high pressure separator in the hydrocracking plant; and
collecting the branches of the heated buffer fluid in a buffer fluid collection header.

13. The method of claim 12, wherein the first heat exchanger, the second heat exchanger and the third heat exchanger are fluidically coupled to each other in parallel.

14. The method of claim 13, further comprising directly heating the stream, wherein directly heating the stream comprises:
heating, in heat exchanger A, a branch of the naphtha splitter bottoms stream using a diesel stripper overhead stream in the diesel hydro-treating plant;
heating, in heat exchanger B, a branch of the naphtha splitter column bottom stream in the aromatics complex benzene extraction unit using a branch of the raffinate column overheads stream;
heating, in heat exchanger C, a branch of the naphtha splitter bottoms stream using the product stripper stream in the hydrocracking plant;
heating, in heat exchanger D, a branch of the naphtha splitter bottoms stream using the diesel product stream in the hydrocracking plant;
heating, in heat exchanger E, a branch of the naphtha splitter bottoms stream using the kerosene product cooling stream from the main fractionator column in the hydrocracking plant; and
heating, in heat exchanger F, a branch of the naphtha splitter bottoms stream using the kerosene pumparound stream in the hydrocracking plant.

15. The method of claim 14, wherein the branches of the naphtha splitter bottoms stream are flowed in parallel to the heat exchanger A, the heat exchanger B, the heat exchanger C, the heat exchanger D, the heat exchanger E and the heat exchanger F.

16. The method of claim 15, further comprising:
flowing heated buffer fluid from the buffer fluid collection header to the aromatics complex benzene extraction unit, the sour water stripper plant, the sulfur recovery plant, the amine regeneration plant and the gas separation plant;
heating, in a fourth heat exchanger, the benzene column bottoms stream in the aromatics complex benzene extraction unit using a branch of the heated buffer fluid;
heating, in a fifth heat exchanger, the raffinate splitter bottoms stream in the aromatics complex benzene extraction unit using a branch of the heated buffer fluid;
heating, in a sixth heat exchanger, the stripper bottoms stream in the sour water stripper plant using a branch of the heated buffer fluid;
heating, in a seventh heat exchanger, the amine regenerator bottoms stream in the sulfur recovery plant using a branch of the heated buffer fluid;
heating, in an eighth heat exchanger, the acid gas regenerator bottoms stream in the amine regeneration plant using a branch of the heated buffer fluid;
heating, in a ninth heat exchanger, the C3/C4 splitter bottom stream in the gas separation plant using a branch of the heated buffer fluid; and
heating, in a tenth heat exchanger, the de-ethanizer column bottoms stream in the gas separation plant using a branch of the heated buffer fluid.

17. The method of claim 16, wherein the heated buffer fluid is flowed first to the aromatics complex benzene extraction unit, then to the sour water stripper plant, then to the sulfur recovery plant, then to the amine regeneration plant, and then to the gas separation plant.

18. The method of claim 17, further comprising flowing the heated buffer fluid exiting the tenth heat exchanger to a buffer fluid tank.

19. The method of claim 14, wherein the heat exchanger A, the heat exchanger B, the heat exchanger C, the heat exchanger D, the heat exchanger E and the heat exchanger F are fluidically coupled to each other in parallel.

20. The method of claim 12, wherein the raffinate column overheads stream requires no additional cooling.

21. The method of claim 20, wherein a portion of the raffinate column overheads stream is cooled by indirectly heating using the first heat exchanger and a portion of the raffinate column overheads stream is cooled by direct heating using the heat exchanger B.

22. The method of claim 12, wherein a cooling requirement of the extract column overheads stream is substantially 0 MW.

* * * * *